United States Patent
Croteau et al.

(10) Patent No.: US 9,175,347 B2
(45) Date of Patent: Nov. 3, 2015

(54) GENOMIC MARKERS FOR PREDICTION OF LONG-TERM RESPONSE TO GROWTH HORMONE (GH) THERAPY

(75) Inventors: Pascal Croteau, Laval (CA); John Raelson, Hudson Heights (CA); Jerome Wojcik, Divonne les Bains (FR); Benoît Destenaves, Peron (FR); Clement Olivier, Geneva (CH); Sonia Schnieper-Samec, Geneva (CH)

(73) Assignee: MERCK SERONO SA, Coinsins, Vaud (CH)

( * ) Notice: Subject to any disclaimer, the term of this patent is extended or adjusted under 35 U.S.C. 154(b) by 3 days.

(21) Appl. No.: 13/819,058

(22) PCT Filed: Aug. 31, 2011

(86) PCT No.: PCT/EP2011/064951
§ 371 (c)(1),
(2), (4) Date: Feb. 26, 2013

(87) PCT Pub. No.: WO2012/028633
PCT Pub. Date: Mar. 8, 2012

(65) Prior Publication Data
US 2013/0157952 A1 Jun. 20, 2013

(30) Foreign Application Priority Data
Aug. 31, 2010 (EP) .................................. 10174732

(51) Int. Cl.
C12Q 1/68 (2006.01)
C12P 19/34 (2006.01)

(52) U.S. Cl.
CPC ............ *C12Q 1/6883* (2013.01); *C12Q 1/6876* (2013.01); *C12Q 1/6886* (2013.01); *C12Q 2600/106* (2013.01); *C12Q 2600/156* (2013.01); *G01N 2800/38* (2013.01); *G01N 2800/52* (2013.01)

(58) Field of Classification Search
None
See application file for complete search history.

(56) References Cited

FOREIGN PATENT DOCUMENTS

WO WO 2010/060935 6/2010

OTHER PUBLICATIONS

Ss5187798 (dbSNP for rs933360; NCBI, NLM, 2002).*
Wan, L. et al. "Growth Hormone (GH) Receptor C.1319 G>T Polymorphism, But Not Exon 3 Retention or Deletion is Associated With Better First-Year Growth Response to GH Therapy in Patients With GH Deficiency" *Pediatric Research*, Dec. 2007, pp. 735-740, vol. 62, No. 6.
Glad, C. A. M. et al. "Rapid and high throughput genotyping of the growth hormone receptor exon 3 deleted/full-length polymorphism using a tagSNP" *Growth Hormone & IGF Research*, Jun. 1, 2010, pp. 270-273, vol. 20, No. 3.
Omokanye, A. et al. "Influence of JAK2 and PI3kinase genotypes on growth response to growth hormone (GH) therapy" *Endocrine Abstracts*, Mar. 2009, pp. 1-2, vol. 19. No. P204.
Fuu-Jen, T. et al. "Pharmacogenetic Study on Efficacy of Recombinant Growth Hormone Treatment in Short Stature Patients with Growth Hormone Deficiency" XP002604843, Jun. 28, 2010, pp. 1-6, Retrieved from the Internet: URL:http://ir.cmu.edu.tw/ir/handle/310903500/25053.
Ranke, M. B. et al. "Predicting growth in response to growth hormone treatment" *Growth Hormone & IGF Research*, Feb. 1, 2009, pp. 1-11, vol. 19, No. 1.
Rosenfeld, R. G. "The Future of Research into Growth Hormone Responsiveness" *Hormone Research*, Apr. 1, 2009, pp. 71-74, vol. 71 (supp).
Binder, G. et al. "The d3-Growth Hormone (GH) Receptor Polymorphism is Associated with Increased Responsiveness to GH in Turner Syndrome and Short Small-for-Gestational-Age Children" *The Journal of Clinical Endocrinology & Metabolism*, 2006, pp. 659-664, Vo. 91, No. 2.

* cited by examiner

*Primary Examiner* — Jehanne Sitton
(74) *Attorney, Agent, or Firm* — Saliwanchik, Lloyd & Eisenschenk

(57) ABSTRACT

The present invention relates to the use of genetic markers to identify the response to growth hormone treatment in Growth Hormone Deficiency (GHD) or Turner Syndrome (TS) patients as well as a method of treating GHD or TS patients and kits for genotyping.

2 Claims, No Drawings

GENOMIC MARKERS FOR PREDICTION OF LONG-TERM RESPONSE TO GROWTH HORMONE (GH) THERAPY

CROSS-REFERENCE TO RELATED APPLICATION

This application is the U.S. national stage application of International Patent Application No. PCT/EP2011/064951, filed Aug. 31, 2011, the disclosure of which is hereby incorporated by reference in its entirety, including all figures, tables and amino acid or nucleic acid sequences.

FIELD OF THE INVENTION

The present invention relates, generally, to pharmacogenetics, more specifically to genetic markers associated with the clinical response to Growth Hormone in Growth Hormone Deficiency (GHD) or Turner Syndrome (TS). The present invention more particularly relates to human genes, which can be used for the diagnosis and treatment of Growth Hormone Deficiency (GHD) or Turner Syndrome (TS).

The invention further discloses specific polymorphisms or alleles of several genes that are related to GHD or TS response to one year GH treatment as well as diagnostic tools and kits based on these susceptibility alterations. Thus, the invention can be used in the diagnosis or detection of the presence, risk or predisposition to, as well as in the prevention and/or treatment of GHD or TS and in predicting the response to growth hormone (GH) treatment.

BACKGROUND OF THE INVENTION

Growth Hormone Deficiency (GHD) includes a group of different pathologies all with a failure or reduction of growth hormone (GH) secretion. GHD may occur by itself or in combination with other pituitary hormone deficiencies. It may be congenital or acquired as a result of trauma, infiltrations, tumour or radiation therapy. Despite the large number of possible aetiologies, most children have idiopathic GHD. Depending on the criteria for diagnosis, the incidence of short stature associated with severe childhood GHD has been estimated to range between 1:4000 to 1:10000 live children in several studies (PC Sizonenko et al., Growth Horm IGF Res 2001; 11(3):137-165).

Postnatal growth of children with GHD differs according to aetiology. Genetic deficiency of GHD causes progressive slowing of growth following normal growth in the first months of life. Growth failure is the major presenting sign of GHD in children, and lack of GH therapy in the case of severe GHD leads to very short stature in adulthood (GH Research Society, J. Clin. Endocrinol Metabol 2000; 85(11): 3990-3993).

Turner (or Ullrich-Turner) syndrome (TS) is a chromosomal abnormality characterized by the absence of the entire chromosome X or a deletion within that chromosome. TS affects one in 1,500 to 2,500 live-born females. Short stature and reduced final height are observed in 95% of girls with TS. The average difference between mean adult height of normal women and that of TS adults is of 20 cm (Park E. et al, Pediatr Res 1983; 17:1-7). Reduced final height is due to a decline in height velocity after the age of 5 or 6 years (relative to unaffected girls) and to the absence of a pubertal growth spurt (Brook C G D et al., Arch Dis Child 1974; 49:789-795) due to the lack of the normal increase in GH secretion observed during puberty. The short stature in TS is not attributable to deficient secretions of GH or insulin-like growth factor I (IGF-I) (Cuttlet L et al., J Clin Endocrinol Metab 1985; 60:1087-1092), but a decreased amplitude and frequency of GH pulses have been reported after the age of 8 years in these patients (Ross J L et al., J Pediatr 1985; 106:202-206).

Recombinant DNA-derived human growth hormone (GH) is the only drug approved specifically for treatment of childhood growth failure and short stature, such as GHD, SGA (Small for Gestational Age) and TS. Current dose regimens for childhood GH therapy are based on body weight and are derived primarily from empirical experience. Variability in individual growth response to weight-based dosing in pediatric indications has led to a search for methods to optimise dosing based on other physiologic parameters. Models for prediction of GH treatment response have thus far relied on biochemical, demographic and anthropometric measures and can account for up to ~70% of the first-year growth in response to rGH.

However, the potential additional effects of genetic variability have not been fully explored. There is thus a need to define a set of genetic/genomic markers associated with short term GH treatment response that could complement the previously identified auxological and biochemical parameters to increase the accuracy with which response to GH treatment could be predicted.

SUMMARY OF THE INVENTION

According to one aspect of the invention, a method is provided for identifying in an individual suffering from Growth Hormone Deficiency or Turner Syndrome, the level of response after the first year of treatment, using annualized clinical endpoints related to the efficacy of growth hormone treatment.

According to another aspect of the invention, a method is provided for treating Growth Hormone Deficiency or Turner Syndrome comprising genotyping the Growth Hormone Deficiency or Turner Syndrome patient and adjusting treatment of the Growth Hormone Deficiency or Turner Syndrome patient based upon the results of the genotyping.

According to another aspect of the invention, a kit is provided for detecting a genetic marker or a combination of genetic markers that is or are associated with the level of response to one year of growth hormone treatment in an individual suffering from Growth Hormone Deficiency or Turner Syndrome.

DETAILED DESCRIPTION OF THE INVENTION

The present invention provides novel approaches to the detection, diagnosis and monitoring of GHD and TS in a subject, as well as for genotyping of patients having GHD or TS. The invention further provides novel approaches to the treatment of GHD and TS in a subject, and to predicting the response to growth hormone (GH) treatment thereby enabling the adjustment of the necessary dose of GH in a patient individualized manner.

Current medications to stimulate linear growth with GH in GHD and TS include SAIZEN®. The active ingredient of SAIZEN® is somatropin, a recombinant human growth hormone (rhGH) produced by genetically engineered mammalian cells (mouse C127). Somatropin is a single-chain, non-glycosylated protein of 191 amino acids with two disulphide bridges.

SAIZEN® is registered in many regions in the following pediatric indications:
growth failure in children caused by decreased or absent secretion of endogenous growth hormone growth failure in children due to causes other than GHD (Turner Syndrome, growth disturbance in short children born SGA)

growth failure in prepubertal children due to chronic renal failure.

SAIZEN® is also registered in 42 countries, including 15 European countries and Switzerland, in the indication of "pronounced growth hormone deficiency" in the adult.

The term "growth hormone (GH)", as used herein, is intended to include growth hormone in particular of human origin, as obtained by isolation from biological fluids or as obtained by DNA recombinant techniques from prokaryotic or eukaryotic host cells, as well as its salts, functional derivatives, variants, analogs and active fragments.

GH is a hormone with pleiotropic effects that result from the complex mechanisms regulating its synthesis and secretion as well as from the GH downstream effects resulting in the activation or inhibition of a variety of different intracellular signaling pathways, responsible for different biological effects of GH. At the cellular level, GH binds to one single receptor, but activates multiple responses within individual target cells. GH-responsive genes include IGF-I which is the major mediator of GH action on somatic growth, and also other proteins involved in the regulation of the metabolic effects of GH. Upon administration of exogenous GH, the effects on somatic growth are long-term, but in the short term they can be evaluated by a variety of markers in peripheral blood that reflect the onset of its biological action.

Recombinant human growth hormone can typically be administered to children in a daily dosage ranging from about 0.02 mg/kg/d of body weight up to about 0.07 mg/kg/d of body weight. This dosage may be given daily or accumulated as weekly dose, or the accumulated weekly dose be split into 3 or 6 equal doses per week.

The response to GH treatment, short-term as well as long-term, displays considerable inter individual variability. This is particularly evident for the endpoint of pediatric GH administration, i.e. the growth response, which varies significantly between subjects with TS but is also pronounced between children who are affected by GHD.

This variability can be investigated at two different levels. First, at the level of clinical endpoints related to the assessment of the individual growth response to GH administration and commonly used in the clinical management of short stature subjects. Secondly, at the genotype level, which can be investigated by identifying the genetic factors responsible for the variation of the above clinical endpoints associated to the response to GH intervention.

Growth prediction models attempt to predict the individual response to GH treatment based on either pre-treatment characteristics and/or on response after a short period of GH administration in comparison to the group response. Pre-treatment parameters used in existing prediction models for idiopathic GHD and Turner Syndrome children receiving GH therapy include auxological criteria, indices of endogenous GH secretion, biological markers of GH action such as insulin-like growth factors (IGF) and their binding proteins (IGFBP), and bone turnover markers.

A clear definition of growth response after intervention with GH is lacking and criteria for defining satisfactory GH response targets are yet to be developed (Bakker et al, J. Clin. Endo. Metabol., 2008). Increase in height and change in height velocity are useful in clinical practice to assess the response to GH (GH research society, J. Clin. Endo. Metabol., 2000). Accurate determination of height velocity, continue to be the most important parameters in monitoring the response to treatment (Wetterau & Cohen, Horm Res, 2000), and these changes as compared to relevant population standards, SDS values. hGH administration is well documented to induce adipose tissue lipolysis (Richelsen B., Horm Res., 1997). It has been shown that adipose tissue mass is significantly reduced in GHD children (Leger et al, J Clin Endo Metabol, 1998). The change in the Body Mass Index, or BMI, a simple anthropometric method to measure changes adiposity, has been shown to be significantly greater in GHD children than in non-GHD (Tillmann et al, Clin. Endo., 2000).

The range of GH response is however rather large and these differences can be attributed to various factors including molecular, biochemical and genetic factors. In the scope of the current patent application, a series of candidate genes were examined that were linked to the GH receptor mechanism, to the postreceptor signaling cascade and the robustness of this cascade, to IGF-I or GH transcriptional and translational efficiency and to other candidates linked to the downstream physiological effects of GH administration.

Response to GH treatment is evaluated herein through several quantitative growth related endpoints. These are Change in Height in cm from Baseline, Change in Height SDS from Baseline, Height Velocity SDS and Change in BMI SDS from Baseline.

Baseline according to this invention is defined as the patient's clinical and biological characteristics before treatment initiation.

In recent years pharmacogenomics—inclusive of pharmacogenetics, as described in the present patent application—(PGx) has come into focus of physicians. Pharmacogenetics can be viewed as the study of inter-individual variations in DNA sequence as related to drug response. In this context the genome of an individual is analyzed leading to the description of genetic markers or susceptibility alterations of significance in this regard. According to the present invention, the variability of the GH response was assessed by detecting genetic determinants potentially linked with Change in Height in cm from Baseline, Change in Height SDS from Baseline, Height Velocity SDS and Change in BMI SDS from Baseline in GH-treated GHD or TS children (genotyping). This approach is of relevance not only in evaluating the efficacy of response to GH treatment but also the treatment's safety profile and long-term consequences. It has been documented that potential side effects of GH treatment include changes in insulin insensitivity and thus the development of impaired glucose tolerance, which can be monitored and depicted by standard clinical and laboratory measures. Within this context, the identification of the genetic determinants will allow prediction of individual response to GH administration and thus stratify the patients for drug administration.

To understand the genetic factors that underlie heritable diseases or the response to pharmacological treatment, classical genetics examines a single gene or a group of a few genes of interest in relation to the trait associated to the heritable diseases or the response to pharmacological treatment. Genomics, on the other hand, allows performance of this search for genetic determinants that result in particular phenotypic characteristics at the level of the entire genome. In the present study, the following genomic techniques were used:

Genotyping: through the identification of DNA variations, this method was used to detect genetic determinants in candidate genes that are potentially linked with GHD, TS or different response rates to GH treatment in these two diseases. The search for DNA variants was performed using single nucleotide polymorphisms (SNPs) as genetic markers.

A SNP is a DNA locus at which the DNA sequence of two individuals carrying distinct alleles differs by one single nucleotide.

SNPs are the most common human genetic polymorphisms and their density on the genome is very high. Nearly 1.8 million SNPs have been discovered and characterized so far and are publicly available in several major databases (see Worldwide Website: hapmap.org, October 2004). Identification of the SNPs of interest according to this invention can be performed with a method developed by Affymetrix or a comparable technique (Matsuzaki H et al., Genome Research 2004; 14:414-425). An association between a genetic marker (or a set of genetic markers called a haplotype) and a disease or response to treatment (the phenotype) indicates that a disease- or response-susceptibility gene may lie in the vicinity of the marker. This association is detected as a statistically significant difference in the frequency of a particular allele or genotype at an SNP locus (or the difference in frequency of a haplotypes over several contiguous SNP loci) between patient groups with different phenotypes. This association can be detected either considering the heterozygote and homozygote status of the alleles for a given SNP, the so-called genotypic association, or on the basis of the presence of one or the other of the allele for a given SNP, the so-called allelic association. These association analyses are carried out using non parametric statistical methods, the Kruskal-Wallis test for genotypic and the Mann Whitney test for allelic association with a quantitative variable.

Once a SNP has been found to be associated to a disease or response to treatment, categorical predictive analysis is required to further determine which allele is best associated to the response to treatment, and thus could serve as a predictive marker. This categorical analysis is carried out with Fisher exact test to examine the significance of the association between two variables, the response (low or high) and the genotype, in a 2×2 contingency table. In a further validation of these findings, the intermediate population is integrated and the tests are rerun this time in a 2×3 contingency table.

Moreover, predictive genetic markers are selected based on a Fisher p-value, corrected for multiple testing, that is less than or equal to 5% and a positive predictive value threshold equal to or greater than 40% or a negative predictive value threshold equal to or greater than 90%. Genetic allele frequency in the study population must be equal to or greater than 15%.

Relative Risks together with the associated confidence interval indicated in brackets are reported as well as the predictive positive values.

The effects of the combined diplotypes for combinations of 2 individual genetic markers were also considered. This is equivalent of the "and" term of Boolean logic.

Complementary categorical analyses can be performed for significant markers, considering the overall population, defined by three groups: Low responders, High responders, and Intermediate group (being neither Low nor High).

The terms "trait" and "phenotype" may be used interchangeably and refer to any clinically distinguishable, detectable or otherwise measurable property of an organism such as symptoms of, or susceptibility to a disease for example. Typically the terms "trait" or "phenotype" are used to refer to symptoms of, or susceptibility to GHD or TS; or to refer to an individual's response to a drug acting against GHD or TS.

As used herein, the term "allele" refers to one of the variant forms of a biallelic or multiallelic alteration, differing from other forms in its nucleotide sequence. Typically the most frequent identified allele is designated as the major allele whereas the other allele(s) are designated as minor allele(s). Diploid organisms may be homozygous or heterozygous for an allelic form.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A polymorphism may comprise a substitution, deletion or insertion of one or more nucleotides. A SNP is a single base pair change. Typically a single nucleotide polymorphism is the replacement of one nucleotide by another nucleotide at the polymorphic site.

As will be discussed below in more details, the alteration ("susceptibility alteration") in a gene or polypeptide according to the invention may be any nucleotide or amino acid alteration associated to the response to growth hormone (GH) treatment in GHD or TS children.

A genotypic marker is defined by an association between response and a genotype or pair of genotypes. These can be the dominance test (carrier of major allele, homozygous and heterozygous, vs. non-carrier of major allele, homozygous minor allele) or the recessive test, (carrier of minor allele, homozygous and heterozygous, vs. non carrier of minor allele, homozygous major allele).

Candidate markers are assessed for their significance in both continuous genetic analyses and categorical analyses in the whole study population separated in a GHD population and a TS population.

A trait associated polymorphism may be any form of mutation(s), deletion(s), rearrangement(s) and/or insertion(s) in the coding and/or non-coding region of the gene, either isolated or in various combination(s). Mutations more specifically include point mutations. Deletions may encompass any region of one or more residues in a coding or non-coding portion of the gene. Typical deletions affect small regions, such as domains (introns) or repeated sequences or fragments of less than about 50 consecutive base pairs, although larger deletions may occur as well. Insertions may encompass the addition of one or several residues in a coding or non-coding portion of the gene. Insertions may typically comprise an addition of between 1 and 50 base pairs in the gene. Rearrangements include for instance sequence inversions. An alteration may also be an aberrant modification of the polynucleotide sequence, and may be silent (i.e., create no modification in the amino acid sequence of the protein), or may result, for instance, in amino acid substitutions, frameshift mutations, stop codons, RNA splicing, e.g. the presence of a non-wild type splicing pattern of a messenger RNA transcript, or RNA or protein instability or a non-wild type level of the polypeptide. Also, the alteration may result in the production of a polypeptide with altered function or stability, or cause a reduction or increase in protein expression levels.

Typical susceptibility alterations or genetic markers are SNPs as described above.

The presence of an alteration in a gene may be detected by any technique known per se to the skilled artisan, including sequencing, pyrosequencing, selective hybridisation, selective amplification and/or mass spectrometry including matrix-assisted laser desorption/ionization time-of-flight mass spectrometry (MALDI-TOF MS). In a particular embodiment, the alteration is detected by selective nucleic acid amplification using one or several specific primers. The alteration is detected by selective hybridization using one or several specific probes.

Further techniques include gel electrophoresis-based genotyping methods such as PCR coupled with restriction fragment length polymorphism (RFLP) analysis, multiplex PCR, oligonucleotide ligation assay, and minisequencing; fluorescent dye-based genotyping technologies such as oligonucleotide ligation assay, pyrosequencing, single-base extension with fluorescence detection, homogeneous solution hybridization such as TaqMan, and molecular beacon genotyping; rolling circle amplification and Invader assays as well as DNA chip-based microarray and mass spectrometry genotyping technologies.

Protein expression analysis methods are known in the art and include 2-dimensional gel-electrophoresis, mass spectrometry and antibody microarrays.

Sequencing can be carried out using techniques well known in the art, e.g. using automatic sequencers. The sequencing may be performed on the complete gene or, more preferably, on specific domains thereof, typically those known or suspected to carry deleterious mutations or other alterations.

Amplification may be performed according to various techniques known in the art, such as by polymerase chain reaction (PCR), ligase chain reaction (LCR) and strand displacement amplification (SDA). These techniques can be performed using commercially available reagents and protocols. A preferred technique is allele-specific PCR.

The term "gene" as used herein shall be construed to include any type of coding nucleic acid region, including genomic DNA (gDNA), complementary DNA (cDNA), synthetic or semi-synthetic DNA, any form of corresponding RNA (e.g., mRNA), etc., as well as non coding sequences, such as introns, 5'- or 3'-untranslated sequences or regulatory sequences (e.g., promoter or enhancer), etc. The term gene particularly includes recombinant nucleic acids, i.e., any non naturally occurring nucleic acid molecule created artificially, e.g., by assembling, cutting, ligating or amplifying sequences. A gene is typically double-stranded, although other forms may be contemplated, such as single-stranded. Genes may be obtained from various sources and according to various techniques known in the art, such as by screening DNA libraries or by amplification from various natural sources. Recombinant nucleic acids may be prepared by conventional techniques, including chemical synthesis, genetic engineering, enzymatic techniques, or a combination thereof. The term "gene" may comprise any and all splicing variants of said gene.

The term "polypeptide" designates, within the context of this invention, a polymer of amino acids without regard to the length of the polymer; thus, peptides, oligopeptides, and proteins are included within the definition of polypeptide. A fragment of a polypeptide designates any portion of at least 8 consecutive amino acids of a sequence of said protein, preferably of at least about 15, more preferably of at least about 20, further preferably of at least 50, 100, 250, 300 or 350 amino acids. This term also includes post-translational or post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides variants which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "treat" or "treating" as used herein is meant to ameliorate, alleviate symptoms, eliminate the causation of the symptoms either on a temporary or permanent basis, or to prevent or slow the appearance of symptoms of the named disorder or condition. The term "treatment" as used herein also encompasses the term "prevention of the disorder", which is, e.g., manifested by delaying the onset of the symptoms of the disorder to a medically significant extent. Treatment of the disorder is, e.g., manifested by a decrease in the symptoms associated with the disorder or an amelioration of the reoccurrence of the symptoms of the disorder.

"Response" to growth hormone treatment in an individual suffering from GHD or TS in the sense of the present invention is understood to be residual disease activity upon a period of approximately one year of growth hormone treatment, with the clinical endpoints annualized. More specifically the residual disease activity is herein associated to Change in Height in cm from Baseline, Change in Height SDS from Baseline, Height Velocity SDS and Change in BMI SDS from Baseline.

"High responders" or "good responders" refer to those individuals who can be identified to show improved response to one year of growth hormone treatment in comparison to the GHD or TS population who exhibit an average response level upon one year of growth hormone treatment. The "high response" or "good response" is exhibited by reduced residual disease activity.

"Low responders" or "poor responders" refers to those individuals who can be identified to show impaired response to one year of growth hormone treatment in comparison to the GHD or TS population who exhibit an average response level upon one year of growth hormone treatment. "High responders" or "good responders" refers to those individuals who can be identified to show increased response to one year of growth hormone treatment in comparison to the GHD or TS population who exhibit an average response level upon one year of growth hormone treatment.

The present invention stems from the pharmacogenomics analysis evaluating gene variations in a group of 310 GHD and TS patients.

In the specific examples as disclosed in the present patent application, extreme categories required for categorical genetic analyses are defined by quartiles:

the low responders are herein represented by the first and lower quartile (designated as Q1) also designated by the lowest 25% of the data (25th percentile);

the high responders are herein represented by the third quartile and upper quartile (designated as Q3) also designated by the highest 75% (75th percentile);

the intermediate group is herein represented as the data from >Q1 and <Q3 also designated as the intermediary 50% of the data.

These quartiles were defined by taking into consideration the age group of patients.

The present invention is directed in a first embodiment to a method of identifying the Change in Height in cm from Baseline in response to treatment with growth hormone in an individual having Growth Hormone Deficiency, the method comprising the steps of:

a. determining in a DNA sample of the individual whether in GRB10 rs933360 either of the CC or TC genotype is present; and b. predicting from the presence of the CC or TC genotype in GRB10 rs933360 an intermediate or low Change in Height in cm from Baseline.

The present invention is also directed to a method of identifying the Change in Height in cm from Baseline in response to treatment with growth hormone in an individual having Growth Hormone Deficiency, the method comprising the steps of:
  a. determining in a DNA sample of the individual whether in SOS1 rs2888586 the CC genotype is present; and
  b. predicting from the presence of the CC genotype in SOS1 rs2888586 an intermediate or low Change in Height in cm from Baseline.

The present invention is also directed to a method of identifying the Change in Height in cm from Baseline in response to treatment with growth hormone in an individual having Growth Hormone Deficiency, the method comprising the steps of:
  a. determining in a DNA sample of the individual whether in CYP19A1 rs10459592 the GG genotype is present; and
  b. predicting from the presence of the GG genotype in CYP19A1 rs10459592 a high Change in Height in cm from Baseline.

The present invention is also directed to a method of identifying the Change in Height in cm from Baseline in response to treatment with growth hormone in an individual having Growth Hormone Deficiency, the method comprising the steps of:
  a. determining in a DNA sample of the individual whether in GRB10 rs4521715 either of the GG or AG genotype is present; and
  b. predicting from the presence of either of the GG or AG genotype in GRB10 rs4521715 an intermediate or low Change in Height in cm from Baseline.

The present invention is also directed to a method of identifying the Change in Height in cm from Baseline in response to treatment with growth hormone in an individual having Growth Hormone Deficiency, the method comprising the steps of:
  a. determining in a DNA sample of the individual whether in IGF2 rs3213221 the CC genotype is present; and
  b. predicting from the presence of the CC genotype in IGF2 rs3213221 a high Change in Height in cm from Baseline.

The present invention is also directed to a method of identifying the Change in Height in cm from Baseline in response to treatment with growth hormone in an individual having Growth Hormone Deficiency, the method comprising the steps of:
  a. determining in a DNA sample of the individual whether in SOS2 rs13379306 either of the AA or AC genotype is present; and
  b. predicting from the presence of the AA or AC genotype in SOS2 rs13379306 a low Change in Height in cm from Baseline.

In another embodiment the present invention is directed to a method of identifying the Change in Height SDS from Baseline in response to treatment with growth hormone in an individual having Growth Hormone Deficiency, the method comprising the steps of:
  a. determining in a DNA sample of the individual whether in GRB10 rs7777754 the GG genotype is present; and
  b. predicting from the presence of the GG genotype in GRB10 rs7777754 an intermediate or low Change in Height SDS from Baseline.

The present invention is also directed to a method of identifying the Change in Height SDS from Baseline in response to treatment with growth hormone in an individual having Growth Hormone Deficiency, the method comprising the steps of:
  a. determining in a DNA sample of the individual whether in SOS1 rs2888586 the CC genotype is present; and
  b. predicting from the presence of the CC genotype in SOS1 rs2888586 a low Change in Height SDS from Baseline.

The present invention is also directed to a method of identifying the Change in Height SDS from Baseline in response to treatment with growth hormone in an individual having Growth Hormone Deficiency, the method comprising the steps of:
  a. determining in a DNA sample of the individual whether in IGF2 rs3213221 the CC genotype is present; and
  b. predicting from the presence of the CC genotype in IGF2 rs3213221 a high Change in Height SDS from Baseline.

In another embodiment the present invention is directed to a method of identifying the Height Velocity SDS in response to treatment with growth hormone in an individual having Growth Hormone Deficiency, the method comprising the steps of:
  a. determining in a DNA sample of the individual whether in GHRHR rs2267723 the GG genotype is present; and
  b. predicting from the presence of the GG genotype in GHRHR rs2267723 an intermediate or low Height Velocity SDS.

The present invention is also directed to a method of identifying the Height Velocity SDS in response to treatment with growth hormone in an individual having Growth Hormone Deficiency, the method comprising the steps of:
  a. determining in a DNA sample of the individual whether in IGFBP3 rs3110697 the AA genotype is present; and
  b. predicting from the presence of the AA genotype in IGFBP3 rs3110697 an intermediate or low Height Velocity SDS.

The present invention is also directed to a method of identifying the Height Velocity SDS in response to treatment with growth hormone in an individual having Growth Hormone Deficiency, the method comprising the steps of:
  a. determining in a DNA sample of the individual whether in CYP19A1 rs700518 the CC genotype is present; and
  b. predicting from the presence of the CC genotype in CYP19A1 rs700518 a high Height Velocity SDS.

The present invention is also directed to a method of identifying the Height Velocity SDS in response to treatment with growth hormone in an individual having Growth Hormone Deficiency, the method comprising the steps of:
  a. determining in a DNA sample of the individual whether in CYP19A1 rs767199 the AA genotype is present; and
  b. predicting from the presence of the AA genotype in CYP19A1 rs767199 a high Height Velocity SDS.

The present invention is also directed to a method of identifying the Height Velocity SDS in response to treatment with growth hormone in an individual having Growth Hormone Deficiency, the method comprising the steps of:
  a. determining in a DNA sample of the individual whether in CYP19A1 rs4545755 the AA genotype is present; and
  b. predicting from the presence of the AA genotype in CYP19A1 rs4545755 a high Height Velocity SDS.

The present invention is also directed to a method of identifying the Height Velocity SDS in response to treatment with growth hormone in an individual having Growth Hormone Deficiency, the method comprising the steps of:
  a. determining in a DNA sample of the individual whether in CYP19A1 rs10459592 the GG genotype is present; and
  b. predicting from the presence of the GG genotype in CYP19A1 rs10459592 a high Height Velocity SDS.

The present invention is also directed to a method of identifying the Height Velocity SDS in response to treatment with growth hormone in an individual having Growth Hormone Deficiency, the method comprising the steps of:
 a. determining in a DNA sample of the individual whether in HRAS rs11246176 either of the GG or AG genotype is present; and
 b. predicting from the presence of the GG or AG genotype in HRAS rs11246176 a high Height Velocity SDS.

The present invention is also directed to a method of identifying the Height Velocity SDS in response to treatment with growth hormone in an individual having Growth Hormone Deficiency, the method comprising the steps of:
 a. determining in a DNA sample of the individual whether in IGF2 rs3213221 the CC genotype is present; and
 b. predicting from the presence of the CC genotype in IGF2 rs3213221 a high Height Velocity SDS.

In another embodiment the present invention is directed to a method of identifying the Change in BMI SDS from Baseline in response to treatment with growth hormone in an individual having Growth Hormone Deficiency, the method comprising the steps of:
 a. determining in a DNA sample of the individual whether in SOCS2 rs1498708 either of the TT or TC genotype is present; and
 b. predicting from the presence of the TT or TC genotype in SOCS2 rs1498708 an intermediate or low Change in BMI SDS from Baseline.

The present invention is also directed to a method of identifying the Change in BMI SDS from Baseline in response to treatment with growth hormone in an individual having Growth Hormone Deficiency, the method comprising the steps of:
 a. determining in a DNA sample of the individual whether in PIK3R2 rs2267922 the GG genotype is present; and
 b. predicting from the presence of the GG genotype in PIK3R2 rs2267922 a high Change in BMI SDS from Baseline.

The present invention is also directed to a method of identifying the Change in BMI SDS from Baseline in response to treatment with growth hormone in an individual having Growth Hormone Deficiency, the method comprising the steps of:
 a. determining in a DNA sample of the individual whether in IRS1 rs2288586 either of the CC or CG genotype is present; and
 b. predicting from the presence of the CC or CG genotype in IRS1 rs2288586 a low Change in BMI SDS from Baseline.

The present invention is also directed to a method of identifying the Change in BMI SDS from Baseline in response to treatment with growth hormone in an individual having Growth Hormone Deficiency, the method comprising the steps of:
 a. determining in a DNA sample of the individual whether in PIK3CD rs4846192 the GG genotype is present; and
 b. predicting from the presence of the GG genotype in PIK3CD rs4846192 a high Change in BMI SDS from Baseline.

The present invention is also directed to a method of identifying the Change in BMI SDS from baseline in response to treatment with growth hormone in an individual having Growth Hormone Deficiency, the method comprising the steps of:
 a. determining in a DNA sample of the individual whether in PIK3R1 rs2161120 the GG genotype is present; and
 b. predicting from the presence of the GG genotype in PIK3R1 rs2161120 an intermediate or high Change in BMI SDS from Baseline.

The present invention is also directed to a method of identifying the Change in BMI SDS from Baseline in response to treatment with growth hormone in an individual having Growth Hormone Deficiency, the method comprising the steps of:
 a. determining in a DNA sample of the individual whether in GHR rs4130113 the GG genotype is present; and
 b. predicting from the presence of the GG genotype in GHR rs4130113 a low Change in BMI SDS from Baseline.

In another embodiment the present invention is directed to a method of identifying the Change in Height in cm from Baseline in response to treatment with growth hormone in an individual having Turner Syndrome, the method comprising the steps of:
 a. determining in a DNA sample of the individual whether in LHX4 rs3845395 either of the CC or GC genotype is present; and
 b. predicting from the presence of either of the CC or GC genotype in LHX4 rs3845395 a high Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in LHX4 rs3845395 the GG genotype is present; and
 b. predicting from the presence of the GG genotype in LHX4 rs3845395 an intermediate or low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in CDK4 rs2069502 either of the TT or TC genotype is present; and
 b. predicting from the presence of either of the TT or TC genotype in CDK4 rs2069502 a high Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in CDK4 rs2069502 the CC genotype is present; and
 b. predicting from the presence of the CC genotype in CDK4 rs2069502 an intermediate or low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in LHX4 rs4652492 the GG genotype is present; and
 b. predicting from the presence of the GG genotype in LHX4 rs4652492 an intermediate or low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in TGFB1 rs4803455 the CC genotype is present; and
 b. predicting from the presence of the CC genotype in TGFB1 rs4803455 an intermediate or low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in SOS1 rs2168043 either of the AA or AC genotype is present; and
 b. predicting from the presence of the AA or AC genotype in SOS1 rs2168043 a high Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in PIK3R3 rs809775 the TT genotype is present; and
 b. predicting from the presence of the TT genotype in PIK3R3 rs809775 a low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in PPP1CB rs6725177 the CC genotype is present; and
 b. predicting from the presence of the CC genotype in PPP1CB rs6725177 a low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in IGFBP3 rs3110697 the GG genotype is present; and
 b. predicting from the presence of the GG genotype in IGFBP3 rs3110697 a low Change in Height in cm from Baseline.

The present invention is also directed to a method of identifying the Change in Height in cm from Baseline in response to treatment with growth hormone in an individual having Turner Syndrome, the method comprising the steps of:
 a. determining in a DNA sample of the individual whether in MYOD1 rs3911833 either of the TT or TC genotype is present; and
 b. predicting from the presence of the TT or TC genotype in MYOD1 rs3911833 an intermediate or high Change in Height in cm from Baseline.

In another embodiment the present invention is directed to a method of identifying the Change in Height SDS from Baseline in response to treatment with growth hormone in an individual having Turner Syndrome, the method comprising the steps of:
 a. determining in a DNA sample of the individual whether in IRS4 rs2073115 either of the TT, TC or T-genotype is present; and
 b. predicting from the presence of the TT, TC or T-genotype in IRS4 rs2073115 a high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in RB1 rs9568036 the GG genotype is present; and
 b. predicting from the presence of the GG genotype in RB1 rs9568036 a high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs2038526 either of the TT or TC genotype is present; and
 b. predicting from the presence of the TT or TC genotype in PTPN1 rs2038526 a low Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs2038526 the CC genotype is present; and
 b. predicting from the presence of the CC genotype in PTPN1 rs2038526 an intermediate or high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs13041704 either of the CC or AC genotype is present; and
 b. predicting from the presence of the CC or AC genotype in PTPN1 rs13041704 a low Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs13041704 the AA genotype is present; and
 b. predicting from the presence of the AA genotype in PTPN1 rs13041704 an intermediate or high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs1570179 the CC genotype is present; and
 b. predicting from the presence of the CC genotype in PTPN1 rs1570179 an intermediate or high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs914460 the TT genotype is present; and
 b. predicting from the presence of the TT genotype in PTPN1 rs914460 an intermediate or high Change in Height SDS from Baseline.

The present invention is also directed to a method of identifying the Change in Height SDS from Baseline in response to treatment with growth hormone in an individual having Turner Syndrome, the method comprising the steps of:
 a. determining in a DNA sample of the individual whether in PTPN1 rs3787335 either of the GG or TG genotype is present; and
 b. predicting from the presence of the GG or TG genotype in PTPN1 rs3787335 a low Change in Height SDS from Baseline.

In another embodiment, the present invention is directed to a method of identifying the Height Velocity SDS in response to treatment with growth hormone in an individual having Turner Syndrome, the method comprising the steps of:
  a. determining in a DNA sample of the individual whether in ESR1 rs2347867 the GG genotype is present; and
  b. predicting from the presence of the GG genotype in ESR1 rs2347867 a high Height Velocity SDS.

The present invention is also directed to a method of identifying the Height Velocity SDS in response to treatment with growth hormone in an individual having Turner Syndrome, the method comprising the steps of:
  a. determining in a DNA sample of the individual whether in IRS4 rs2073115 either of the TT, TC or T-genotype is present; and
  b. predicting from the presence of the TT, TC or T-genotype in IRS4 rs2073115 a high Height Velocity SDS.

The present invention is also directed to a method of identifying the Height Velocity SDS in response to treatment with growth hormone in an individual having Turner Syndrome, the method comprising the steps of:
  a. determining in a DNA sample of the individual whether in JAK2 rs7034753 the AA genotype is present; and
  b. predicting from the presence of the AA genotype in JAK2 rs7034753 a low Height Velocity SDS.

The present invention is also directed to a method of identifying the Height Velocity SDS in response to treatment with growth hormone in an individual having Turner Syndrome, the method comprising the steps of:
  a. determining in a DNA sample of the individual whether in RB1 rs9568036 the GG genotype is present; and
  b. predicting from the presence of the GG genotype in RB1 rs9568036 a high Height Velocity SDS.

The present invention is also directed to a method of identifying the Height Velocity SDS in response to treatment with growth hormone in an individual having Turner Syndrome, the method comprising the steps of:
  a. determining in a DNA sample of the individual whether in SREBF1 rs9899634 the AA genotype is present; and
  b. predicting from the presence of the AA genotype in SREBF1 rs9899634 a low Height Velocity SDS.

In another embodiment, the present invention is directed to a method of identifying the Change in BMI SDS from Baseline in response to treatment with growth hormone in an individual having Turner Syndrome, the method comprising the steps of:
  a. determining in a DNA sample of the individual whether in TGFA rs378322 either of the AA or AG genotype is present; and
  b. predicting from the presence of the AA or AG genotype in TGFA rs378322 a low Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs12958785 the GG genotype is present; and
  b. predicting from the presence of the GG genotype in BCL2 rs12958785 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs12958785 either of the AA or AG genotype is present; and
  b. predicting from the presence of the AA or AG genotype in BCL2 rs12958785 an intermediate or low Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in CYP19A1 rs767199 the AA genotype is present; and
  b. predicting from the presence of the AA genotype in CYP19A1 rs767199 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs1531695 the TT genotype is present; and
  b. predicting from the presence of the TT genotype in BCL2 rs1531695 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs4987792 the GG genotype is present; and
  b. predicting from the presence of the GG genotype in BCL2 rs4987792 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs744569 the AA genotype is present; and
  b. predicting from the presence of the AA genotype in BCL2 rs744569 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in BCL2 rs731014 the TT genotype is present; and
  b. predicting from the presence of the TT genotype in BCL2 rs731014 a high Change in BMI SDS from Baseline.

The present invention is also directed to a method of identifying the Change in BMI SDS from Baseline in response to treatment with growth hormone in an individual having Turner Syndrome, the method comprising the steps of:
  a. determining in a DNA sample of the individual whether in ESR1 rs7761846 either of the CC or TC genotype is present; and
  b. predicting from the presence of the CC or TC genotype in ESR1 rs7761846 a low Change in BMI SDS from Baseline.

The present invention is also directed to a method of identifying the Change in BMI SDS from Baseline in response to treatment with growth hormone in an individual having Turner Syndrome, the method comprising the steps of:

a. determining in a DNA sample of the individual whether in STAT cluster rs2293152 the CC genotype is present; and
b. predicting from the presence of the CC genotype in STAT cluster rs2293152 an intermediate or low Change in BMI SDS from Baseline.

The present invention is also directed to a method of identifying the Change in BMI SDS from Baseline in response to treatment with growth hormone in an individual having Turner Syndrome, the method comprising the steps of:
a. determining in a DNA sample of the individual whether in SH2B2 rs803090 either of the AA or AG genotype is present; and
b. predicting from the presence of the AA or AG genotype in SH2B2 rs803090 a high Change in BMI SDS from Baseline.

In all the above sections, A, T, C and G represent adenine, thymine, cytosine and guanine, respectively.

DNA samples according to the present invention may be obtained by taking blood samples from an individual.

Preferably, the treatment with growth hormone has been carried out during about 1 year. In a further embodiment the present invention is directed to a kit for detecting a genetic markers or a combination of genetic markers that are associated with the level of response to treatment with growth hormone, as previously stated in association to biomarker response to GH treatment and in this particular case to IGF-I response.

The kit comprises a probe or a set of oligonucleotide primers designed for identifying each of the alleles in any of the above described genetic variants Probes and primers that can be used according to the invention preferably are fragments of sequences or hybridize to the sequences shown to be associated with Change in Height in cm from Baseline, Change in Height SDS from Baseline, Height Velocity SDS and Change in BMI SDS from Baseline in response to one year of GH treatment.

The results according to this invention may be applied in approaches of personalized medicine. Personalized medicine is, according to the present patent application, the use of information and data from a patient's genotype to stratify disease, select a medication, provide a therapy, or initiate a preventative measure that is particularly suited to that patient at the time of administration. In addition to genetic information, other factors, including imaging, laboratory, and clinical information about the disease process or the patient play an equally important role. It is believed that personalized medicine will make it possible in the future to give the appropriate drug, at the appropriate dose, to the appropriate patient, at the appropriate time.

Since the data generated by the present study documents a correlation between growth response to human Growth Hormone (hGH) treatment and the presence of specific genetic variants carried by human patients, the present invention aims at covering body growth resulting of cellular, tissular or somatic growth in human patients modulated or regulated (up or down regulated) by hGH treatment through this variant; in addition the invention aims at covering the use for treatment (and or even diagnostic) purpose of either natural hGH, recombinant hGH, hGH analogs (agonists or antagonists, natural or non natural regardless of their mode of production) acting through this specific genetic variant to modulate growth response in human patients.

Patients with a genotype predictive of a high response can be given the standard dose of GH, i.e. the dose currently used in clinical practice, which is for children a daily dosage ranging from about 0.02 mg/kg of body weight up to about 0.07 mg/kg of body weight. Alternatively these patients can be given an optimized dose. Patients with markers predictive of a low response would be given an optimized dose of GH or an analog thereof. An optimized dose of GH to be given to a low responder may be an increased dose of GH compared to the standard dose as a dose-response relationship in terms of height velocity in the first 2 years of treatment has been demonstrated; and this in a dose range compatible with the fixed dose used to treat GHD or TS patients in the current settings. Low responders can also be candidate patients for therapies with long acting analogs of GH with a frequency of administration which is decreased.

In a further embodiment the present invention is thus directed to a method for treating Growth Hormone Deficiency (GHD) or Turner Syndrome (TS) in an individual in need thereof, the method comprising the steps of:
a. identifying the level of response to treatment with growth hormone according to any of the methods described above,
b. treating the individual with growth hormone.

In a preferred embodiment, the individual is identified as low responder and is treated with a dose of growth hormone that is optimized compared to the standard dose.

In one embodiment, a low responder is treated with a dose of growth hormone that is increased compared to the standard dose or he is treated with a long-acting analog of growth hormone.

Genetic markers were identified herein as being associated to low or high response, the response herein described being the Change in Height in cm from Baseline, Change in Height SDS from Baseline, Height Velocity SDS and Change in BMI SDS from Baseline after one year of GH treatment. These genetic markers can be considered either alone or in combination in the methods according to the invention.

In a further embodiment, the invention relates to the use of growth hormone in the preparation of a medicament for treating pediatric Growth Hormone Deficiency (GHD) or Turner Syndrome (TS) in an individual in need thereof, wherein the individual has been identified according to any of the methods described above to be a low responder or a high responder to the treatment with growth hormone.

In a further embodiment, the present invention relates also to growth hormone for use in treating pediatric Growth Hormone Deficiency (GHD) or Turner Syndrome (TS) in an individual in need thereof, wherein the individual has been identified according to any of the methods described above to be a low responder or a high responder to the treatment with growth hormone.

In the method of identifying, kit or method of treating according to the invention the growth hormone is preferably human growth hormone and more preferably recombinant human growth hormone. Particular embodiments of the invention refer to growth hormone as sold under the tradename SAIZEN®.

Formulations useful in a method of treating a GHD or TS patient according to the invention may be a liquid pharmaceutical formulation comprising growth hormone or a reconstituted freeze-dried formulation comprising growth hormone. Preferably the formulation is stabilized by a polyol, more preferably a disaccharide and even more preferably sucrose.

In the following the present invention shall be illustrated by means of the following examples that are not to be construed as limiting the scope of the invention.

EXAMPLES

Example 1

Genotyping 1.1. Background

GHD and TS and the different auxological responses to GH treatment in the two diseases may each be associated with a specific genetic variation in one or several genes. In the present study, the search for associations between genes containing variations, in the present invention SNPs, so-called susceptibility genes, and disease or response to treatment was focused on candidate genes that were selected based on the physiological role of the proteins they encode and their potential implication in the diseases, GHD and TS, or in the response to GH treatment. The list of selected candidate genes is given in Table 1.

Response to GH treatment was measured by Change in Height in cm from Baseline, Change in Height SDS from Baseline, Height Velocity SDS and Change in BMI SDS from Baseline in response to 1 year of treatment with GH.

TABLE 1

| GHD OR TS RELATED GENES | |
|---|---|
| FGF-R3 | GH-1 |
| GH-R | GHRH |
| GHRH-R | Glut4 |
| HESX-1 | IGF-1 |
| Insulin-VNTR LHX3 | LHX4 |
| POU1F1 (Pit-1) | Prop-1 |
| SHOX-1 | SHOX-2 |
| STAT-5 | |
| GH & IGF-1 RELATED GENES | |
| ALS | APS (SH2B2) |
| β Arrestin-1 (ARRB1) | GAB-1 |
| GH1 | GH-R |
| GHRH | GHRH-R |
| ID1 & ID2 | IGF-I |
| IGF-I-R | IGF-II |
| IGF-II-R | IGF-BP3 |
| IGF-BP1 | IGF-BP-2 |
| IGF-BP10 | JAK2 |
| MAP Kinase | PGDF-Rβ |
| PTP1β (PTPN1) | PI3Kinase subunits |
| p60dok | SHC1 |
| STAT-5 | SOCS-2 |
| STAT-3 | GRB10 |
| SHPS-1 | SH2B2 |
| INSULIN RELATED GENES | |
| Adiponectin (Acrp30 or AdipoQ) | ADRβ3) |
| AKT 1 & AKT 2 | Glut4 |
| Glut1 also known as SLCA1 | GRB2 |
| Insulin (VNTR) | Insulin-R |
| IRS-1 | IRS-2 |
| IRS-4 | LEP (leptin) |
| LEP-R (Leptin-R) (Ob-R) | pp120/HA4 (CEACAM8) |
| PI3Kinase p85 | PI3Kinase p110 α and p110β (polymorphic GATA binding site) Protein-Phosphatase 1 (PP1) |
| PTP1β | PDK1 |
| PPAR γ | PPARγCo-activator1 (PGC1) |
| RAs | SHIP2 |
| SHC1 | SOS 1 & 2 |
| SREBP-1c | TNFα |
| BONE METABOLISM RELATED GENES | |
| AR | Aromatase |
| ER-α | GPCRs |
| Myogenin | MyoD |
| p21 | PKCα |
| RA-R | |

TABLE 1-continued

| ONCOGENES & INFLAMMATORY RELATED GENES | |
|---|---|
| bcl-2 | c-Erb B1 |
| c-fos | c-jun |
| jun-b | c-myc |
| CDK2 CDK4 and CDK6 | Cyclin D |
| TGF-α | TGF-β |
| p53 | Ras |
| Rb | WT1 |
| INFLAMMATION RELATED GENES | |
| GATA1 | IL-4 |
| IL-6 | TNF-α |

The candidate genes selected have been previously implicated in growth, the mechanism of action of growth hormone, or in growth hormone deficiency or Turner syndrome. The purpose of the study was to investigate whether TS, GHD in association to Change in Height in cm from Baseline, Change in Height SDS from Baseline, Height Velocity SDS and Change in BMI SDS from Baseline in response to one year of GH treatment in these diseases is correlated with a specific DNA variant or pattern of variants. The existence of such a correlation would indicate that either the gene(s) carrying the identified variant(s) or one or more genes lying in the vicinity of the variants may be (a) susceptibility gene(s).

1.2. Materials and Methods 1.2.1. DNA Samples Extraction and Preparation

The analysis was performed on DNA extracted from polymorphonuclear leucocytes. A total of 319 blood samples were received. Out of these 319, 3 samples were not double coded and were destroyed by the genomic laboratory. The 316 samples remaining went into the genomic analysis. Out of these 316 DNA samples analysed, 3 were duplicates resulting in 313 DNAs analysed corresponding to 313 patients in the Predict study. Upon transfer of the clinical data, 3 patients with DNA analysed did not have any clinical data collected.

Thus 310 patients were genotyped and eligible for the association studies.

Regarding the year one analysis of the follow-up study, 310 patients were genotyped and eligible for the association studies. Only 170 consented to participate to the follow-up study after the initial interventional one month study. 60 TS and 110 GHD have the baseline and the year one auxological values required for the association described in the present patent application.

DNA was extracted from 316 blood samples between November 2006 and November 2007 using a Qiagen kit (QIAamp DNA Blood Midi Kit/Lot 127140243/Ref 51185). After extraction DNA quality and quantity were controlled (QC.1 and QC.2) by measures of absorbance at wavelengths of 260 nm and 280 nm using a (Molecular Devices Spectramax Plus) spectrophotometer and electrophoresis of DNA samples on agarose gels.

QC.1: 260 nm/280 nm absorbance ratio and DNA concentration calculated from the 280 nm absorbance value.

QC.2: Electrophoresis on agarose gel.

All 316 DNA samples passed the acceptance criteria defined for QC.1: absorbance ratio between 1.7 and 2.1 and DNA concentration above 50 ng/μL All 316 DNA samples passed the acceptance criteria defined for QC.2: for each sample, one clearly defined band visible on agarose gel after electrophoresis at a high molecular weight corresponding to non-degraded genomic DNA.

An aliquot of 3 μg of DNA from each sample was distributed into four 96 well micro-plates. Each micro-plate also contained a negative control and a reference genomic DNA (referred to as DNA 103).

The four micro-plates were assigned a name ranging from Saizen-PL1 to Saizen-PL4. The 316 samples were assigned a genotyping number ranging from 50-1657 to 50-1972.

1.2.2. DNA Microarray Technology

DNA microarray technology was used for genotyping. A microarray is an experimental tool that was developed to meet the needs of whole genome analysis to simultaneously screen a vast number of genes or gene products Due to its miniaturised format and amenability to automation, a microarray is suitable for high-throughput analysis. The technique is based on the ability of two nucleic acid molecules to selectively bind (hybridise) to one another if their sequences are complementary. A set of different nucleic acid fragments, the probe, is covalently attached at defined positions on a solid support of a few square centimeters. The genetic material to be analysed, the target, is exposed to the arrayed probe. Using the selective hybridisation property of nucleic acids, the probes are designed in such a way that they will bind only to those target molecules that are of interest in the particular investigation. Selective labelling of the bound complex and the knowledge of the identity of each probe based on its location on the array allows the identification of the target molecule.

In this experiment, the Illumina GoldenGate technology protocol was used. This technology is based on 3 micron silica beads that self assemble in micro-wells on either of two substrates, fiber optic bundles or planar silica slides. When randomly assembled on one of these two substrates, the beads had a uniform spacing of ~5.7 microns. Each bead is covered with hundreds of thousands of copies of a specific oligonucleotide that act as capture sequences.

1536 SNPs were selected from 103 candidate genes and 1448 SNPs were successfully genotyped for all individuals and analysed in 97 candidate genes out of these 1448 SNPs.

The samples were randomly distributed by the biobanking technician on four 96-well microplate. Each microplate was then processed sequentially using a different Illumina kit and Sentrix Array Matrix for each plate.

1.2.3. Genetics Analysis

For continuous quantitative data, The R version 2.9.0 software (R: A language and environment for statistical computing) was used for data analysis to perform quantitative association analysis. The "kruskal.test" function was used to perform non-parametric Kruskal-Wallis sign rank test of single marker.

For Categorical analyses, association analysis software algorithms for single marker association analysis, for sex chromosome linked copy number association analyses, for haplotype association analyses and for analysis of all two marker diplotype combinations were used.

Only the available data was integrated in the analysis, no imputation was carried out.

1.2.4. Estimation of Linkage Disequilibrium (LD) Structure

The number of Linkage Disequilibrium (LD) blocks in each gene was estimated in the two disease groups by means of the "ALLELE" SAS procedure, through the JMP Genomics interface. This was used to compute adjusted p-values.

1.2.5. Statistical Testing

Continuous Analyses

For a given phenotype at year one (Change in Height in cm, Change in Height SDS, Height Velocity SDS and Change in BMI SDS), new variables were built, indicating major and minor allele presence.

Genotypic Association

The association between the genotype and the phenotypic quantitative variable was evaluated by the Kruskal-Wallis association test implemented by the 'kruskal.test' function of the R software package. The main output of this procedure was a table essentially giving the probability levels (p-values) for the genotype categorical effect on phenotype, for each SNP and disease group.

Allelic Association

Similarly, the association between the presence of the major allele and the biomarker quantitative variable was also evaluated by the Kruskal-Wallis association test implemented by the 'kruskal.test' function of the R software package. The same was repeated for the minor allele.

The output of these procedures was a table essentially giving the p-values for the effect on phenotype of the presence of the corresponding allele, for ach SNP and disease group.

Selection of Significantly Associated SNPs and Genes

Two summary tables were produced to join output of the association tests performed (p-value and nature of the corresponding genetic variable) together with disease type, SNP and gene names, number of SNPs tested and of LD blocks in the gene, and SNP minor allele frequency (MAF) and call rate.

For selection of significant associations, Bonferroni correction for multiple testing was applied to compute adjusted p-values based on the number of tested LD blocks in the same gene (Table 4A; nominal p-value).

An initial aggressive selection of genes containing SNPs eligible for association was performed by selecting observations where the MAF was greater than 0.1, so as to have a frequency of the minor allele frequency (MAF) above 10% (Table 4B; MAF), the call rate greater than 0.95, and the initial, unadjusted p-value was lower than the nominal 0.05 significance cut-off.

The final selection of significantly associated genes was based on adjustment of the nominal marker p-values by the number of LD-blocks (Table 4A; adjusted p-values), used as an estimate of the number of independent tests applied to each gene.

Relevant information:

R version: 2.9.0

R citation:

R Development Core Team (2009). R: A language and environment for statistical computing. R Foundation for Statistical Computing, Vienna, Austria. ISBN 3-900051-07-0, URL http://www.R-project.org.

Categorical Analysis: Prediction

A selection of SNPs were assessed for potential use in patient stratification and association with the following auxological endpoint parameters at year one: Change in Height in cm from Baseline, Change in Height SDS from Baseline, height velocity SDS and Change in Body Mass Index (BMI) SDS from Baseline. These qualitative continuous variables were classified into categories which were analyzed as 2×2 contingency tables using Fisher's exact test for the chi-square statistic.

Good responders were defined as having values for each of the four endpoint variables that were greater than or equal to the $3^{rd}$ quartile of the distribution for each variable.

Poor responders, were defined has having values for each of the 4 endpoint variables that were less than or equal to the $1^{st}$ quartile of the distribution for each variable.

Intermediate responders were defined as having values for each of the 4 endpoint variables that were less than Q3 and greater than Q1.

Quartiles were calculated independently for each of 3 age groups within each of the endpoint variables. The upper ($3^{rd}$) and lower ($1^{st}$) Quartile values are given in Table 1B below.

Quartiles were defined by taking into consideration the age group as well.

TABLE 1B

Quartile Thresholds for Different Age Groups within Four Auxological one year endpoints for GHD and TS children.

| subject | Age group | upper 25% cutoff | lower 25% cutoff | Total N | N high | N Low | N intermediate |
|---|---|---|---|---|---|---|---|
| \multicolumn{8}{l}{Change in Height from in cm From Baseline AUHTCGCM)} |
| GHD | <8 Yrs | 11.14 | 7.88 | 37 | 10 | 10 | 17 |
| GHD | >=8 yrs, <=12 yrs | 9.465 | 6.9 | 56 | 14 | 14 | 28 |
| GHD | >12 yrs | 10.54 | 7.31 | 17 | 5 | 5 | 7 |
| GHD | Total N | | | 110 | 29 | 29 | 52 |
| GHD | Total % | | | 100 | 26.364 | 26.364 | 47.273 |
| TS | <8 Yrs | 9.31 | 7.18 | 22 | 6 | 6 | 10 |
| TS | >=8 yrs, <=12 yrs | 9.225 | 6.635 | 28 | 7 | 7 | 14 |
| TS | >12 yrs | 6.42 | 5.26 | 10 | 3 | 3 | 4 |
| | Total N | | | 60 | 16 | 16 | 28 |
| | Total % | | | 100 | 26.667 | 26.667 | 46.667 |
| \multicolumn{8}{l}{Height Velocity SDS (AUHVSDS)} |
| GHD | <8 Yrs | 6.3 | 2.61 | 37 | 10 | 10 | 17 |
| GHD | >=8 yrs, <=12 yrs | 3.11 | 0.47 | 56 | 15 | 14 | 27 |
| GHD | >12 yrs | 1.72 | 0.16 | 17 | 5 | 5 | 7 |
| GHD | Total N | | | 110 | 30 | 29 | 51 |
| GHD | Total % | | | 100 | 27.273 | 26.364 | 46.364 |
| TS | <8 Yrs | 4.1 | 1.45 | 22 | 6 | 6 | 10 |
| TS | >=8 yrs, <=12 yrs | 1.875 | 0.515 | 28 | 7 | 7 | 14 |
| TS | >12 yrs | 7.31 | 1.2 | 10 | 3 | 3 | 4 |
| | Total N | | | 60 | 16 | 16 | 28 |
| | Total % | | | 100 | 26.667 | 26.667 | 46.667 |
| \multicolumn{8}{l}{Change in Height SDS From Baseline (AUHCGSDS)} |
| GHD | <8 Yrs | 1.36 | 0.51 | 37 | 10 | 10 | 17 |
| GHD | >=8 yrs, <=12 yrs | 0.78 | 0.375 | 56 | 15 | 14 | 27 |
| GHD | >12 yrs | 0.81 | 0.02 | 17 | 5 | 5 | 7 |
| GHD | Total N | | | 110 | 30 | 29 | 51 |
| GHD | Total % | | | 100 | 27.273 | 26.364 | 46.364 |
| TS | <8 Yrs | 0.82 | 0.48 | 22 | 6 | 6 | 10 |
| TS | >=8 yrs, <=12 yrs | 0.68 | 0.155 | 28 | 7 | 7 | 14 |
| TS | >12 yrs | 0.75 | 0.09 | 10 | 3 | 3 | 4 |
| | Total N | | | 60 | 16 | 16 | 28 |
| | Total % | | | 100 | 26.667 | 26.667 | 46.667 |
| \multicolumn{8}{l}{Change in BMI SDS From Baseline (AUBSDSCG)} |
| GHD | <8 Yrs | 0.585 | −0.355 | 36 | 9 | 9 | 18 |
| GHD | >=8 yrs, <=12 yrs | 0.19 | −0.29 | 56 | 14 | 15 | 27 |
| GHD | >12 yrs | 0.14 | −0.36 | 17 | 5 | 5 | 7 |
| GHD | Total N | | | 109 | 28 | 29 | 52 |
| GHD | Total % | | | 100 | 25.688 | 26.606 | 47.706 |
| TS | <8 Yrs | 0.04 | −0.76 | 22 | 6 | 6 | 10 |
| TS | >=8 yrs, <=12 yrs | 0.23 | −0.895 | 28 | 7 | 7 | 14 |
| TS | >12 yrs | 0.06 | −0.9 | 10 | 3 | 3 | 4 |
| | Total N | | | 60 | 16 | 16 | 28 |
| | Total % | | | 100 | 26.667 | 26.667 | 46.667 |

Analyses consisted of tests for each of two alternative comparisons, high responders (≥Q3) versus intermediate and low responders (<Q3); and low responders (≤Q1 versus intermediate and high responders (>Q1). Each of the two contrasts was tested using two distinct genetic models, dominance of major allele (Ma) and recessive for major allele. The major allele (Ma) is defined as the more frequent of the two alternative alleles of each DNA marker and the minor allele (Mi) is defined as the less frequent of the two alternative alleles. The two genotype markers for the dominance major allele test are MaMa or MaMi genotypes versus MiMi genotype. The two genotype markers within the recessive major allele test are MaMa versus MiMi or MaMi genotypes. Each of the two alternative genotype markers is associated (more frequent) in one of the two alternative categories for each contrast. Therefore, each genotype marker of the DNA marker is indicative of one of the two alternative categories.

DNA markers were selected as potential biomarkers if they were associated with one of the four endpoint variables at an adjusted (for multiple tests) Fisher exact p-value that was less than or equal to 0.10. In addition to p-value for the tests, the following parameters of the association were also noted:

Relative risk (RR) and the 95% confidence interval for RR: RR is the increase in probability of being a category 1 individual (high or low responder, depending on the contrast tested), given that the individual carries the category 1 associated genotype marker relative to the probability of being a category 1 individual given that the individual carries the alternative genotype marker.

Positive predictive value (PPV): the probability of being a category 1 individual given that the individual carries the category 1 associated genotype marker. The expected value for PPV given no effect is 25%. Increased departures from this level indicate the utility of the biomarker.

Negative predictive value (NPV): the probability of being a category 2 (intermediate or low responder, or intermediate or high responder, depending upon the contrast) individual given that the individual carries the category 2 associated genotype marker. The expected value for NPV given no effect is 75%. Increased departures from this level indicate the utility of the biomarker.

Frequency of the two genotype markers for each biomarker: Values between 15 and 85% for these frequencies indicate a sufficiently frequent marker to be a useful biomarker.

1.3. Results

The purpose of this study was the identification of genetic markers associated to variation of clinical endpoints relevant to growth, herein Change in Height in cm from Baseline, Change in Height SDS from Baseline, Height Velocity SDS and Change in BMI SDS from Baseline annualised and thus reflecting the growth effect of one year of treatment with human recombinant growth hormone in GHD or TS children. Association with Change in Height in Cm from Baseline, Change in Height SDS from Baseline, Height Velocity SDS, and Change in BMI SDS from Baseline Change in Height in cm from Baseline, Change in Height SDS from Baseline, Height Velocity SDS, and Change in BMI SDS from Baseline were considered in this study as the primary markers of growth response.

Association of SNPs in Candidate Genes Through Continuous Analysis

SNPs were tested for association (genotypic, major or minor allele dominance) and the SNPs found to be associated to the above clinical endpoints through these continuous analyses are reported in the below Table 4.

Prediction Analysis of SNPs Through Categorical Analysis

Considering categories of response, significant associations were found for GHD children for a number of SNPs as depictured in Tables 2 and 3.

GHD Children

TABLE 2

Marker SNPs in GHD subjects

AUHTCGCM

| Condition | Endpoint | Marker | Gene | non-parametric adjusted p-value | Categorical Model | Categorical Exact p-value | Categorical Adjusted p-value | Relative Risk | 95% CI Relative Risk |
|---|---|---|---|---|---|---|---|---|---|
| GHD | Height Change in cm | rs933360 | GRB10 | 0.044800 | Recessive | 0.00123 | 0.02590 | 4.76 | [1.54, 14.73] |
| GHD | Height Change in cm | rs2888586 | SOS1 | 0.047600 | Recessive | 0.00859 | 0.04294 | 3.71 | [1.21, 11.42] |
| GHD | Height Change in cm | rs10459592 | CYP19A1 | 0.043000 | Recessive | 0.00303 | 0.04549 | 2.61 | [1.44, 4.71] |
| GHD | Height Change in cm | rs4521715 | GRB10 | 0.100100 | Recessive | 0.00127 | 0.02660 | 4.57 | [1.48, 14.14] |
| GHD | Height Change in cm | rs3213221 | IGF2 | 0.101700 | Dominance | 0.01381 | 0.04142 | 2.46 | [1.36, 4.45] |
| GHD | Height Change in cm | rs13379306 | SOS2 | 0.066700 | Recessive | 0.00602 | 0.04818 | 2.43 | [1.31, 4.49] |

| Condition | Endpoint | Marker | Gene | Category 1 | Category 2 | Genotype Marker for Category 1 | Genotype Marker for Category 2 | Total Frequency of Genotype Marker for Category 1 | Total Frequency of Genotype Marker for Category 2 |
|---|---|---|---|---|---|---|---|---|---|
| GHD | Height Change in cm | rs933360 | GRB10 | H | I + L | TT | CC & TC | 0.6455 | 0.3545 |
| GHD | Height Change in cm | rs2888586 | SOS1 | H | I + L | TT & TC | CC | 0.7000 | 0.3000 |
| GHD | Height Change in cm | rs10459592 | CYP19A1 | H | I + L | GG | TT & TG | 0.2636 | 0.7364 |
| GHD | Height Change in cm | rs4521715 | GRB10 | H | I + L | AA | GG & AG | 0.6545 | 0.3455 |
| GHD | Height Change in cm | rs3213221 | IGF2 | H | I + L | CC | GG & CG | 0.1545 | 0.8455 |
| GHD | Height Change in cm | rs13379306 | SOS2 | L | I + H | AA & AC | CC | 0.3364 | 0.6636 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 individuals among Carriers of Genotype Marker for Category 1 | NPV Frequency of Category 2 individuals among Carriers of Genotype Marker for Category 2 |
|---|---|---|---|---|---|---|---|---|---|
| GHD | Height Change in cm | rs933360 | GRB10 | 26 | 45 | 3 | 36 | 0.3662 | 0.9231 |
| GHD | Height Change in cm | rs2888586 | SOS1 | 26 | 51 | 3 | 30 | 0.3377 | 0.9091 |
| GHD | Height Change in cm | rs10459592 | CYP19A1 | 14 | 15 | 15 | 66 | 0.4828 | 0.8148 |
| GHD | Height Change in cm | rs4521715 | GRB10 | 26 | 46 | 3 | 35 | 0.3611 | 0.9211 |
| GHD | Height Change in cm | rs3213221 | IGF2 | 9 | 8 | 20 | 73 | 0.5294 | 0.7849 |
| GHD | Height Change in cm | rs13379306 | SOS2 | 16 | 21 | 13 | 60 | 0.4324 | 0.8219 |

AUHCGSDS

| Condition | Endpoint | Marker | Gene | non-parametric adjusted p-value | Categorical Model | Categorical Exact p-value | Categorical Adjusted p-value | Relative Risk | 95% CI Relative Risk |
|---|---|---|---|---|---|---|---|---|---|
| GHD | Height Change SDS | rs7777754 | GRB10 | 1 | Recessive | 0.00091 | 0.01901 | 4.01 | [1.51, 10.70] |
| GHD | Height Change SDS | rs2888586 | SOS1 | 0.0671 | Recessive | 0.00450 | 0.02251 | 2.50 | [1.37, 4.57] |
| GHD | Height Change SDS | rs3213221 | IGF2 | 0.2142 | Dominance | 0.01633 | 0.04899 | 2.34 | [1.31, 4.21] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| GHD | Height Change SDS | rs7777754 | GRB10 | H | I + L | TT & TG | GG | 0.6182 | 0.3818 |
| GHD | Height Change SDS | rs2888586 | SOS1 | L | I + H | CC | TT & TC | 0.3000 | 0.7000 |
| GHD | Height Change SDS | rs3213221 | IGF2 | H | I + L | CC | GG & CG | 0.1545 | 0.8455 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| GHD | Height Change SDS | rs7777754 | GRB10 | 26 | 42 | 4 | 38 | 0.3824 | 0.9048 |
| GHD | Height Change SDS | rs2888586 | SOS1 | 15 | 18 | 14 | 63 | 0.4545 | 0.8182 |
| GHD | Height Change SDS | rs3213221 | IGF2 | 9 | 8 | 21 | 72 | 0.5294 | 0.7742 |

TABLE 2-continued

Marker SNPs in GHD subjects

AUHVSDS

| Condition | Endpoint | Marker | Gene | Non-parametric Adjusted p-value | Categorical Model | Categorical Exact p-value | Categorical Adjusted p-value | Relative Risk | 95% CI Relative Risk |
|---|---|---|---|---|---|---|---|---|---|
| GHD | Height Velocity SDS | rs2267723 | GHRHR | 0.028000 | Dominance | 0.00075 | 0.00449 | NA | NA |
| GHD | Height Velocity SDS | rs3110697 | IGFBP3 | 0.001300 | Dominance | 0.00276 | 0.01381 | NA | NA |
| GHD | Height Velocity SDS | rs700518 | CYP19A1 | 1.000000 | Dominance | 0.00049 | 0.00728 | 3.14 | [1.80, 5.49] |
| GHD | Height Velocity SDS | rs767199 | CYP19A1 | 1.000000 | Dominance | 0.00067 | 0.01002 | 3.00 | [1.74, 5.18] |
| GHD | Height Velocity SDS | rs4545755 | CYP19A1 | 1.000000 | Dominance | 0.00102 | 0.01524 | 2.96 | [1.72, 5.10] |
| GHD | Height Velocity SDS | rs10459592 | CYP19A1 | 0.559100 | Recessive | 0.00123 | 0.01842 | 2.79 | [1.57, 4.97] |
| GHD | Height Velocity SDS | rs11246176 | HRAS | 0.127800 | Recessive | 0.01287 | 0.01287 | 2.34 | [1.29, 4.24] |
| GHD | Height Velocity SDS | rs3213221 | IGF2 | 0.226300 | Dominance | 0.01633 | 0.04899 | 2.34 | [1.31, 4.21] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| GHD | Height Velocity SDS | rs2267723 | GHRHR | H | I + L | AA & AG | GG | 0.8091 | 0.1909 |
| GHD | Height Velocity SDS | rs3110697 | IGFBP3 | H | I + L | GG & AG | AA | 0.8349 | 0.1651 |
| GHD | Height Velocity SDS | rs700518 | CYP19A1 | H | I + L | CC | TT & TC | 0.1835 | 0.8165 |
| GHD | Height Velocity SDS | rs767199 | CYP19A1 | H | I + L | AA | GG & AG | 0.1818 | 0.8182 |
| GHD | Height Velocity SDS | rs4545755 | CYP19A1 | H | I + L | AA | GG & AG | 0.1636 | 0.8364 |
| GHD | Height Velocity SDS | rs10459592 | CYP19A1 | H | I + L | GG | TT & TG | 0.2636 | 0.7364 |
| GHD | Height Velocity SDS | rs11246176 | HRAS | H | I + L | GG & AG | AA | 0.1835 | 0.8165 |
| GHD | Height Velocity SDS | rs3213221 | IGF2 | H | I + L | CC | GG & CG | 0.1545 | 0.8455 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| GHD | Height Velocity SDS | rs2267723 | GHRHR | 30 | 59 | 0 | 21 | 0.3371 | 1.0000 |
| GHD | Height Velocity SDS | rs3110697 | IGFBP3 | 30 | 61 | 0 | 18 | 0.3297 | 1.0000 |
| GHD | Height Velocity SDS | rs700518 | CYP19A1 | 12 | 8 | 17 | 72 | 0.6000 | 0.8090 |
| GHD | Height Velocity SDS | rs767199 | CYP19A1 | 12 | 8 | 18 | 72 | 0.6000 | 0.8000 |
| GHD | Height Velocity SDS | rs4545755 | CYP19A1 | 11 | 7 | 19 | 73 | 0.6111 | 0.7935 |
| GHD | Height Velocity SDS | rs10459592 | CYP19A1 | 15 | 14 | 15 | 66 | 0.5172 | 0.8148 |
| GHD | Height Velocity SDS | rs11246176 | HRAS | 10 | 10 | 19 | 70 | 0.5000 | 0.7865 |
| GHD | Height Velocity SDS | rs3213221 | IGF2 | 9 | 8 | 21 | 72 | 0.5294 | 0.7742 |

AUBSDSCG

| Condition | Endpoint | Marker | Gene | Non-Parametric Adjusted p-value | Categorical Model | Categorical Exact p-value | Categorical Adjusted p-value | Relative Risk | 95% CI Relative Risk |
|---|---|---|---|---|---|---|---|---|---|
| GHD | Change in BMI SDS | rs1498708 | SOCS2 | 0.033500 | Recessive | 0.04369 | 0.04369 | 2.95 | [0.97, 9.03] |
| GHD | Change in BMI SDS | rs2267922 | PIK3R2 | 0.060700 | Recessive | 0.01170 | 0.01170 | 2.39 | [1.30, 4.40] |
| GHD | Change in BMI SDS | rs2288586 | IRS1 | 0.056500 | Recessive | 0.01287 | 0.03862 | 2.34 | [1.29, 4.24] |
| GHD | Change in BMI SDS | rs4846192 | PIK3CD | 1.000000 | Recessive | 0.00567 | 0.03972 | 2.51 | [1.37, 4.59] |
| GHD | Change in BMI SDS | rs2161120 | PIK3R1 | 0.055200 | Dominance | 0.00186 | 0.04102 | 8.77 | [1.25, 61.37] |
| GHD | Change in BMI SDS | rs4130113 | GHR | 0.353600 | Recessive | 0.00205 | 0.04500 | 2.71 | [1.48, 4.99] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| GHD | Change in BMI SDS | rs1498708 | SOCS2 | H | I + L | CC | TT & TC | 0.7383 | 0.2617 |
| GHD | Change in BMI SDS | rs2267922 | PIK3R2 | H | I + L | GG | CC & CG | 0.2661 | 0.7339 |
| GHD | Change in BMI SDS | rs2288586 | IRS1 | L | I + H | CC & CG | GG | 0.1835 | 0.8165 |
| GHD | Change in BMI SDS | rs4846192 | PIK3CD | H | I + L | GG | AA & AG | 0.2569 | 0.7431 |

TABLE 2-continued

Marker SNPs in GHD subjects

| Condition | Endpoint | Marker | Gene | | | | | | |
|---|---|---|---|---|---|---|---|---|---|
| GHD | Change in BMI SDS | rs2161120 | PIK3R1 | L | I + H | AA & AG | GG | 0.7615 | 0.2385 |
| GHD | Change in BMI SDS | rs4130113 | GHR | L | I + H | GG | AA & AG | 0.3119 | 0.6881 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| GHD | Change in BMI SDS | rs1498708 | SOCS2 | 25 | 54 | 3 | 25 | 0.3165 | 0.8929 |
| GHD | Change in BMI SDS | rs2267922 | PIK3R2 | 13 | 16 | 15 | 65 | 0.4483 | 0.8125 |
| GHD | Change in BMI SDS | rs2288586 | IRS1 | 10 | 10 | 19 | 70 | 0.5000 | 0.7865 |
| GHD | Change in BMI SDS | rs4846192 | PIK3CD | 13 | 15 | 15 | 66 | 0.4643 | 0.8148 |
| GHD | Change in BMI SDS | rs2161120 | PIK3R1 | 28 | 55 | 1 | 25 | 0.3373 | 0.9615 |
| GHD | Change in BMI SDS | rs4130113 | GHR | 16 | 18 | 13 | 62 | 0.4706 | 0.8267 |

Legend:
Non-parametric adjusted p-value, p-value from Kruskal-Wallis One Way Analysis of Variance by Rank Test adjusted for number of LD blocks tested within the gene.
Categorical models: Dominance test compares carriers of major allele (MaMa or MaMi genotypes) against non-carriers of major allele (MiMi genotype); recessive test compares carriers of minor allele (MaMi or MiMi genotypes) against non-carriers of minor allele (MaMa genotype).
Categorical exact p-value, p-value from Fisher's Exact Test.
Categorical adjusted p-values, p-value from Fisher's Exact Test adjusted by number of LD blocks tested within the gene.
Relative Risk, increased probability of being a Category 1 responder for carriers of the marker genotype compared to carriers of the non-marker genotype.
95% CI Relative Risk, interval within which the true relative risk will lie at a probability of 95%.
Positive Predictive Value (PPV), proportion of Category 1 responders that carry the marker genotype.
Negative Predictive Value (NPV), proportion of Category 2 responders that carry the non-marker genotype.

Carrying the CC or TC genotype for rs933360 in gene GRB10 has a 92% predictive value in GHD children for intermediate or low response based on the one year Change in Height in cm.

Carrying the CC genotype for rs2888586 in gene SOS1 has a 91% predictive value in GHD children for intermediate or low response based on the one year Change in Height in cm.

Carrying the GG genotype for rs10459592 in gene CYP19A1 has a 48% predictive value in GHD children for high response based on the one year Change in Height in cm.

Carrying the GG or AG genotype for rs4521715 in gene GRB10 has a 92% predictive value in GHD children for intermediate or low response based on the one year Change in Height in cm.

Carrying the CC genotype for rs3213221 in gene IGF2 has a 53% predictive value for high response based on the one year Change in Height in cm.

Carrying the AA or AC genotype for rs13379306 in gene SOS2 has a 43% predictive value for low response based on the one year Change in Height in cm.

Carrying the GG genotype for rs7777754 in gene GRB10 has a 90% predictive value for intermediate or low response based on the one year Change in Height SDS.

Carrying the CC genotype for rs2888586 in gene SOS1 has a 45% predictive value for low response based on the one year Change in Height SDS.

Carrying the CC genotype for rs3213221 in gene IGF2 has a 53% predictive value for high response based on the one year Change in Height SDS.

Carrying the GG genotype for rs2267723 in gene GHRHR has a 100% predictive value for intermediate or low response based on the one year Height Velocity SDS.

Carrying the AA genotype for rs3110697 in gene IGFBP3 has a 100 predictive value for intermediate or low response based on the one year Height Velocity SDS.

Carrying the CC genotype for rs700518 in gene CYP19A1 has a 60% predictive value for high response based on the one year Height Velocity SDS.

Carrying the AA genotype for rs767199 in gene CYP19A1 has a 60% predictive value for high response based on the one year Height Velocity SDS.

Carrying the AA genotype for rs4545755 in gene CYP19A1 has a 61% predictive value for high response based on the one year Height Velocity SDS.

Carrying the GG genotype for rs10459592 in gene CYP19A1 has a 52% predictive value for high response based on the one year Height Velocity SDS.

Carrying the GG or AG genotype for rs11246176 in gene HRAS has a 50% predictive value for high response based on the one year Height Velocity SDS.

Carrying the CC genotype for rs3213221 in gene IGF2 has a 53% predictive value for high response based on the one year Height Velocity SDS.

Carrying the TT or TC genotype for rs1498708 in gene SOCS2 has a 89% predictive value for intermediate or low response based on the one year Change in BMI SDS.

Carrying the GG genotype for rs2267922 in gene PIK3R2 has a 45% predictive value for high response based on the one year Change in BMI SDS.

Carrying the CC or CG genotype for rs2288586 in gene IRS1 has a 50% predictive value for low response based on the one year Change in BMI SDS.

Carrying the GG genotype for rs4846192 in gene PIK3CD has a 46% predictive value for high response based on the one year Change in BMI SDS.

Carrying the GG genotype for rs2161120 in gene PIK3R1 has a 96% predictive value for intermediate or high response based on the one year Change in BMI SDS.

Carrying the GG genotype for rs4130113 in gene GHR has a 47% predictive value for low response based on the one year Change in BMI SDS.

TS Children

TABLE 3

Marker SNPs in TS subjects

AUHTCGCM

| Condition | Endpoint | Marker | Gene | Non-Parametric Adjusted p-value | Categorical Model | Categorical Exact p-value | Categorical Adjusted p-value | Relative Risk | 95% CI Relative Risk |
|---|---|---|---|---|---|---|---|---|---|
| TS | Height Change in cm | rs3845395 | LHX4 | 0.048500 | Recessive | 0.00032 | 0.00667 | 7.48 | [1.86, 30.11] |
| TS | Height Change in cm | rs2069502 | CDK4 | 1.000000 | Recessive | 0.00729 | 0.01458 | 5.00 | [1.25, 20.07] |
| TS | Height Change in cm | rs4652492 | LHX4 | 0.617800 | Recessive | 0.00131 | 0.02748 | NA | NA |
| TS | Height Change in cm | rs4803455 | TGFB1 | 0.195500 | Recessive | 0.01265 | 0.03794 | NA | NA |
| TS | Height Change in cm | rs2168043 | SOS1 | 0.154900 | Recessive | 0.00789 | 0.03943 | 3.25 | [1.44, 7.33] |
| TS | Height Change in cm | rs809775 | PIK3R3 | 0.624700 | Recessive | 0.00602 | 0.01806 | 3.29 | [1.51, 7.14] |
| TS | Height Change in cm | rs6725177 | PPP1CB | 1.000000 | Recessive | 0.00598 | 0.02991 | 3.33 | [1.41, 7.86] |
| TS | Height Change in cm | rs3110697 | IGFBP3 | 0.400200 | Recessive | 0.00842 | 0.04212 | 3.30 | [1.31, 8.30] |
| TS | Height Change in cm | rs3911833 | MYOD1 | 0.758900 | Recessive | 0.04758 | 0.04758 | 5.21 | [0.74, 36.47] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| TS | Height Change in cm | rs3845395 | LHX4 | H | I + L | CC & GC | GG | 0.4833 | 0.5167 |
| TS | Height Change in cm | rs2069502 | CDK4 | H | I + L | TT & TC | CC | 0.5833 | 0.4167 |
| TS | Height Change in cm | rs4652492 | LHX4 | H | I + L | AA & AG | GG | 0.7000 | 0.3000 |
| TS | Height Change in cm | rs4803455 | TGFB1 | H | I + L | AA & AC | CC | 0.7667 | 0.2333 |
| TS | Height Change in cm | rs2168043 | SOS1 | H | I + L | AA & AC | CC | 0.2833 | 0.7167 |
| TS | Height Change in cm | rs809775 | PIK3R3 | L | I + H | TT | AA & AT | 0.2333 | 0.7667 |
| TS | Height Change in cm | rs6725177 | PPP1CB | L | I + H | CC | GG & GC | 0.3333 | 0.6667 |
| TS | Height Change in cm | rs3110697 | IGFBP3 | L | I + H | GG | AA & AG | 0.4000 | 0.6000 |
| TS | Height Change in cm | rs3911833 | MYOD1 | L | I + H | CC | TT & TC | 0.7288 | 0.2712 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| TS | Height Change in cm | rs3845395 | LHX4 | 14 | 15 | 2 | 29 | 0.4828 | 0.9355 |
| TS | Height Change in cm | rs2069502 | CDK4 | 14 | 21 | 2 | 23 | 0.4000 | 0.9200 |
| TS | Height Change in cm | rs4652492 | LHX4 | 16 | 26 | 0 | 18 | 0.3810 | 1.0000 |
| TS | Height Change in cm | rs4803455 | TGFB1 | 16 | 30 | 0 | 14 | 0.3478 | 1.0000 |
| TS | Height Change in cm | rs2168043 | SOS1 | 9 | 8 | 7 | 36 | 0.5294 | 0.8372 |
| TS | Height Change in cm | rs809775 | PIK3R3 | 8 | 6 | 8 | 38 | 0.5714 | 0.8261 |
| TS | Height Change in cm | rs6725177 | PPP1CB | 10 | 10 | 6 | 34 | 0.5000 | 0.8500 |
| TS | Height Change in cm | rs3110697 | IGFBP3 | 11 | 13 | 5 | 31 | 0.4583 | 0.8611 |
| TS | Height Change in cm | rs3911833 | MYOD1 | 14 | 29 | 1 | 15 | 0.3256 | 0.9375 |

AUHCGSDS

| Condition | Endpoint | Marker | Gene | Non-Parametric Adjusted p-value | Categorical Model | Categorical Exact p-value | Categorical Adjusted p-value | Relative Risk | 95% CI Relative Risk |
|---|---|---|---|---|---|---|---|---|---|
| TS | Height Change SDS | rs2073115 | IRS4 | 0.053700 | Recessive | 0.00873 | 0.00873 | 3.33 | [1.62, 6.86] |
| TS | Height Change SDS | rs9568036 | RB1 | 0.113700 | Dominance | 0.00795 | 0.03973 | 3.40 | [1.65, 7.00] |
| TS | Height Change SDS | rs2038526 | PTPN1 | 0.334200 | Recessive | 0.00082 | 0.00571 | 10.71 | [1.51, 75.92] |
| TS | Height Change SDS | rs13041704 | PTPN1 | 0.266000 | Recessive | 0.00219 | 0.01530 | 9.32 | [1.32, 65.95] |
| TS | Height Change SDS | rs1570179 | PTPN1 | 0.499900 | Recessive | 0.00277 | 0.01941 | 8.68 | [1.23, 61.34] |
| TS | Height Change SDS | rs914460 | PTPN1 | 0.499900 | Recessive | 0.00277 | 0.01941 | 8.68 | [1.23, 61.34] |
| TS | Height Change SDS | rs3787335 | PTPN1 | 0.062700 | Recessive | 0.00602 | 0.04214 | 3.29 | [1.51, 7.14] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| TS | Height Change SDS | rs2073115 | IRS4 | H | I + L | TT, TC & T- | CC | 0.1525 | 0.8475 |
| TS | Height Change SDS | rs9568036 | RB1 | H | I + L | GG | AA & AG | 0.1500 | 0.8500 |
| TS | Height Change SDS | rs2038526 | PTPN1 | L | I + H | TT & TC | CC | 0.5833 | 0.4167 |
| TS | Height Change SDS | rs13041704 | PTPN1 | L | I + H | CC & AC | AA | 0.6167 | 0.3833 |

TABLE 3-continued

Marker SNPs in TS subjects

| Condition | Endpoint | Marker | Gene | | | | | | | |
|---|---|---|---|---|---|---|---|---|---|---|
| TS | Height Change SDS | rs1570179 | PTPN1 | L | | I + H | TT & TC | CC | 0.6333 | 0.3667 |
| TS | Height Change SDS | rs914460 | PTPN1 | L | | I + H | CC & TC | TT | 0.6333 | 0.3667 |
| TS | Height Change SDS | rs3787335 | PTPN1 | L | | I + H | GG & TG | TT | 0.2333 | 0.7667 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| TS | Height Change SDS | rs2073115 | IRS4 | 6 | 3 | 10 | 40 | 0.6667 | 0.8000 |
| TS | Height Change SDS | rs9568036 | RB1 | 6 | 3 | 10 | 41 | 0.6667 | 0.8039 |
| TS | Height Change SDS | rs2038526 | PTPN1 | 15 | 20 | 1 | 24 | 0.4286 | 0.9600 |
| TS | Height Change SDS | rs13041704 | PTPN1 | 15 | 22 | 1 | 22 | 0.4054 | 0.9565 |
| TS | Height Change SDS | rs1570179 | PTPN1 | 15 | 23 | 1 | 21 | 0.3947 | 0.9545 |
| TS | Height Change SDS | rs914460 | PTPN1 | 15 | 23 | 1 | 21 | 0.3947 | 0.9545 |
| TS | Height Change SDS | rs3787335 | PTPN1 | 8 | 6 | 8 | 38 | 0.5714 | 0.8261 |

AUVSDS

| Condition | Endpoint | Marker | Gene | Non-Parametric Adjusted p-value | Categorical Model | Categorical Exact p-value | Categorical Adjusted p-value | Relative Risk | 95% CI Relative Risk |
|---|---|---|---|---|---|---|---|---|---|
| TS | Height Velocity SDS | rs2347867 | ESR1 | 0.012800 | Dominance | 0.00011 | 0.00501 | 5.14 | [2.41, 10.98] |
| TS | Height Velocity SDS | rs2073115 | IRS4 | 0.060600 | Recessive | 0.00873 | 0.00873 | 3.33 | [1.62, 6.86] |
| TS | Height Velocity SDS | rs7034753 | JAK2 | 1.000000 | Recessive | 0.00388 | 0.03880 | 3.60 | [1.53, 8.44] |
| TS | Height Velocity SDS | rs9568036 | RB1 | 0.081600 | Dominance | 0.00795 | 0.03973 | 3.40 | [1.65, 7.00] |
| TS | Height Velocity SDS | rs9899634 | SREBF1 | 0.786600 | Dominance | 0.04867 | 0.04867 | 2.53 | [1.13, 5.65] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| TS | Height Velocity SDS | rs2347867 | ESR1 | H | I + L | GG | AA & AG | 0.2000 | 0.8000 |
| TS | Height Velocity SDS | rs2073115 | IRS4 | H | I + L | TT & TC | CC | 0.1525 | 0.8475 |
| TS | Height Velocity SDS | rs7034753 | JAK2 | L | I + H | AA | GG & AG | 0.3167 | 0.6833 |
| TS | Height Velocity SDS | rs9568036 | RB1 | H | I + L | GG | AA & AG | 0.1500 | 0.8500 |
| TS | Height Velocity SDS | rs9899634 | SREBF1 | L | I + H | AA | TT & TA | 0.2833 | 0.7167 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| TS | Height Velocity SDS | rs2347867 | ESR1 | 9 | 3 | 7 | 41 | 0.7500 | 0.8542 |
| TS | Height Velocity SDS | rs2073115 | IRS4 | 6 | 3 | 10 | 40 | 0.6667 | 0.8000 |
| TS | Height Velocity SDS | rs7034753 | JAK2 | 10 | 9 | 6 | 35 | 0.5263 | 0.8537 |
| TS | Height Velocity SDS | rs9568036 | RB1 | 6 | 3 | 10 | 41 | 0.6667 | 0.8039 |
| TS | Height Velocity SDS | rs9899634 | SREBF1 | 8 | 9 | 8 | 35 | 0.4706 | 0.8140 |

AUBSDSCG

| Condition | Endpoint | Marker | Gene | Non-Parametric Adjusted p-value | Categorical Model | Categorical Exact p-value | Categorical Adjusted p-value | Relative Risk | 95% CI Relative Ris |
|---|---|---|---|---|---|---|---|---|---|
| TS | Change in BMI SDS | rs378322 | TGFA | 0.018700 | Recessive | 0.00011 | 0.00250 | 5.14 | [2.41, 10.98] |
| TS | Change in BMI SDS | rs12958785 | BCL2 | 0.127000 | Recessive | 0.00006 | 0.00265 | 6.97 | [2.22, 21.85] |
| TS | Change in BMI SDS | rs767199 | CYP19A1 | 1.000000 | Dominance | 0.00169 | 0.02709 | 3.86 | [1.74, 8.55] |
| TS | Change in BMI SDS | rs1531695 | BCL2 | 0.427300 | Recessive | 0.00075 | 0.03134 | 4.83 | [1.77, 13.18] |
| TS | Change in BMI SDS | rs4987792 | BCL2 | 0.427300 | Recessive | 0.00075 | 0.03134 | 4.83 | [1.77, 13.18] |
| TS | Change in BMI SDS | rs744569 | BCL2 | 0.427300 | Recessive | 0.00075 | 0.03134 | 4.83 | [1.77, 13.18] |
| TS | Change in BMI SDS | rs731014 | BCL2 | 0.427300 | Recessive | 0.00075 | 0.03134 | 4.83 | [1.77, 13.18] |
| TS | Change in BMI SDS | rs7761846 | ESR1 | 0.520600 | Recessive | 0.00078 | 0.03442 | 4.22 | [1.93, 9.27] |

TABLE 3-continued

Marker SNPs in TS subjects

| Condition | Endpoint | Marker | Gene | | | | | | |
|---|---|---|---|---|---|---|---|---|---|
| TS | Change in BMI SDS | rs2293152 | STAT_cluster | 0.318800 | Recessive | 0.00531 | 0.03719 | 8.08 | [1.15, 56.97] |
| TS | Change in BMI SDS | rs803090 | SH2B2 | 1.000000 | Recessive | 0.01000 | 0.04998 | 3.43 | [1.25, 9.43] |

| Condition | Endpoint | Marker | Gene | Category 1 | Category 2 | Genotype Marker for Category 1 | Genotype Marker for Category 2 | Total Frequency Genotype Marker for Category 1 | Total Frequency Genotype Marker for Category 2 |
|---|---|---|---|---|---|---|---|---|---|
| TS | Change in BMI SDS | rs378322 | TGFA | L | I + H | AA & AG | GG | 0.2000 | 0.8000 |
| TS | Change in BMI SDS | rs12958785 | BCL2 | H | I + L | GG | AA & AG | 0.3833 | 0.6167 |
| TS | Change in BMI SDS | rs767199 | CYP19A1 | H | I + L | AA | GG & AG | 0.2500 | 0.7500 |
| TS | Change in BMI SDS | rs1531695 | BCL2 | H | I + L | TT | CC & TC | 0.3833 | 0.6167 |
| TS | Change in BMI SDS | rs4987792 | BCL2 | H | I + L | GG | AA & AG | 0.3833 | 0.6167 |
| TS | Change in BMI SDS | rs744569 | BCL2 | H | I + L | AA | GG & AG | 0.3833 | 0.6167 |
| TS | Change in BMI SDS | rs731014 | BCL2 | H | I + L | TT | CC & TC | 0.3833 | 0.6167 |
| TS | Change in BMI SDS | rs7761846 | ESR1 | L | I + H | CC & TC | TT | 0.2333 | 0.7667 |
| TS | Change in BMI SDS | rs2293152 | STAT_cluster | H | I + L | GG & CG | CC | 0.6500 | 0.3500 |
| TS | Change in BMI SDS | rs803090 | SH2B2 | H | I + L | AA & AG | GG | 0.4667 | 0.5333 |

| Condition | Endpoint | Marker | Gene | Number of Category 1 individuals that Carry Genotype Marker for Category 1 | Number of Category 2 individuals that Carry Genotype Marker for Category 1 | Number of Category 1 individuals that Carry Genotype Marker for Category 2 | Number of Category 2 individuals that Carry Genotype Marker for Category 2 | PPV Frequency of category 1 among carriers of Marker for Category 1 | NPV Frequency of Category 2 among carriers of Marker for Category 2 |
|---|---|---|---|---|---|---|---|---|---|
| TS | Change in BMI SDS | rs378322 | TGFA | 9 | 3 | 7 | 41 | 0.7500 | 0.8542 |
| TS | Change in BMI SDS | rs12958785 | BCL2 | 13 | 10 | 3 | 34 | 0.5652 | 0.9189 |
| TS | Change in BMI SDS | rs767199 | CYP19A1 | 9 | 6 | 7 | 38 | 0.6000 | 0.8444 |
| TS | Change in BMI SDS | rs1531695 | BCL2 | 12 | 11 | 4 | 33 | 0.5217 | 0.8919 |
| TS | Change in BMI SDS | rs4987792 | BCL2 | 12 | 11 | 4 | 33 | 0.5217 | 0.8919 |
| TS | Change in BMI SDS | rs744569 | BCL2 | 12 | 11 | 4 | 33 | 0.5217 | 0.8919 |
| TS | Change in BMI SDS | rs731014 | BCL2 | 12 | 11 | 4 | 33 | 0.5217 | 0.8919 |
| TS | Change in BMI SDS | rs7761846 | ESR1 | 9 | 5 | 7 | 39 | 0.6429 | 0.8478 |
| TS | Change in BMI SDS | rs2293152 | STAT_cluster | 15 | 24 | 1 | 20 | 0.3846 | 0.9524 |
| TS | Change in BMI SDS | rs803090 | SH2B2 | 12 | 16 | 4 | 28 | 0.4286 | 0.8750 |

Legend:
Non-parametric adjusted p-value, p-value from Kruskal-Wallis One Way Analysis of Variance by Rank Test adjusted for number of LD blocks tested within the gene.
Categorical models: Dominance test compares carriers of major allele (MaMa or MaMi genotypes) against non-carriers of major allele (MiMi genotype); recessive test compares carriers of minor allele (MaMi or MiMi genotypes) against non-carriers of minor allele (MaMa genotype).
Categorical exact p-value, p-value from Fisher's Exact Test.
Categorical adjusted p-values, p-value from Fisher's Exact Test adjusted by number of LD blocks tested within the gene.
Relative Risk, increased probability of being a Category 1 responder for carriers of the marker genotype compared to carriers of the non-marker genotype.
95% CI Relative Risk, interval within which the true relative risk will lie at a probability of 95%.
Positive Predictive Value (PPV), proportion of Category 1 responders that carry the marker genotype.
Negative Predictive Value (NPV), proportion of Category 2 responders that carry the non-marker genotype.

Carrying the CC or GC genotype for rs3845395 in gene LHX4 has a 48% predictive value in TS children for high response based on the one year Change in Height in cm.

Carrying the GG genotype for rs3845395 in gene LHX4 has a 93% predictive value in TS children for intermediate or low response based on the one year Change in Height in cm.

Carrying the TT or TC genotype for rs2069502 in gene CDK4 has a 40% predictive value in TS children for high response based on the one year Change in Height in cm.

Carrying the CC genotype for rs2069502 in gene CDK4 has a 92% predictive value in TS children for intermediate or low response based on the one year Change in Height in cm.

Carrying the GG genotype for rs4652492 in gene LHX4 has a 100% predictive value for intermediate or low response based on the one year Change in Height in cm.

Carrying the CC genotype for rs4803455 in gene TGFB1 has a 100% predictive value for intermediate or low response based on the one year Change in Height in cm.

Carrying the AA or AC genotype for rs2168043 in gene SOS1 has a 53% predictive value for high response based on the one year Change in Height in cm.

Carrying the TT genotype for rs809775 in gene PIK3R3 has a 57% predictive value for low response based on the one year Change in Height in cm.

Carrying the CC genotype for rs6725177 in gene PPP1CB has a 50% predictive value for low response based on the one year Change in Height in cm.

Carrying the GG genotype for rs3110697 in gene IGFBP3 has a 46% predictive value for low response based on the one year Change in Height in cm.

Carrying the TT or TC genotype for rs3911833 in gene MYOD 1 has a 94% predictive value for intermediate or high response based on the one year Change in Height in cm.

Carrying the TT, TC or T-genotype for rs2073115 in gene IRS4 has a 67% predictive value for high response based on the one year Change in Height SDS.

Carrying the GG genotype for rs9568036 in gene RB1 has a 67% predictive value for high response based on the one year Change in Height SDS.

Carrying the TT or TC genotype for rs2038536 in gene PTPN1 has a 43% predictive value for low response based on the one year Change in Height SDS.

Carrying the CC genotype for rs2038536 in gene PTPN1 has a 96% predictive value for intermediate or high response based on the one year Change in Height SDS.

Carrying the CC or AC genotype for rs13041704 in gene PTPN1 has a 41% predictive value for low response based on the one year Change in Height SDS.

Carrying the AA genotype for rs13041704 in gene PTPN1 has a 96% predictive value for intermediate or high response based on the one year Change in Height SDS.

Carrying the CC genotype for rs1570179 in gene PTPN1 has a 95% predictive value for intermediate or high response based on the one year Change in Height SDS.

Carrying the TT genotype for rs914460 in gene PTPN1 has a 95% predictive value for intermediate or high response based on the one year Change in Height SDS.

Carrying the GG or TG genotype for rs3787335 in gene PTPN1 has a 57% predictive value for low response based on the one year Change in Height SDS.

Carrying the GG genotype for rs2347867 in gene ESR1 has a 75% predictive value for high response based on the one year Height Velocity SDS.

Carrying the TT, TC or T-genotype for rs2073115 in gene IRS4 has a 67% predictive value for high response based on the one year Height Velocity SDS.

Carrying the AA genotype for rs7034753 in gene JAK2 has a 53% predictive value for low response based on the one year Height Velocity SDS.

Carrying the GG genotype for rs9568036 in gene RB1 has a 67% predictive value for high response based on the one year Height Velocity SDS.

Carrying the AA genotype for rs9899634 in gene SREBF1 has a 47% predictive value for low response based on the one year Height Velocity SDS.

Carrying the AA or AG genotype for rs378322 in gene TGFA has a 75% predictive value for low response based on the one year Change in BMI SDS.

Carrying the GG genotype for rs12958785 in gene BCL2 has a 57% predictive value for high response based on the one year Change in BMI SDS.

Carrying the AA or AG genotype for rs12958785 in gene BCL2 has a 92% predictive value for high response based on the one year Change in BMI SDS.

Carrying the AA genotype for rs767199 in gene CYP19A1 has a 60% predictive value for high response based on the one year Change in BMI SDS.

Carrying the TT genotype for rs1531695 in gene BCL2 has a 52% predictive value for high response based on the one year Change in BMI SDS.

Carrying the GG genotype for rs4987792 in gene BCL2 has a 52% predictive value for high response based on the one year Change in BMI SDS.

Carrying the AA genotype for rs744569 in gene BCL2 has a 52% predictive value for high response based on the one year Change in BMI SDS.

Carrying the TT genotype for rs731014 in gene BCL2 has a 52% predictive value for high response based on the one year Change in BMI SDS.

Carrying the CC or TC genotype for rs7761846 in gene ESR1 has a 64% predictive value for low response based on the one year Change in BMI SDS.

Carrying the CC genotype for rs2293152 in the STAT gene cluster has a 95% predictive value for intermediate or low response based on the one year Change in BMI SDS.

Carrying the AA or AG genotype for rs803090 in gene SH2B2 has a 43% predictive value for high response based on the one year Change in BMI SDS.

TABLE 4A

SNPs associated through continuous analysis.

| Condition | SNP ID | Gene | Endpoint | Model | Nominal p-value | Adjusted p-value |
|---|---|---|---|---|---|---|
| GHD | rs5918757 | AR | BMI SDS Change | Dominant | 0.036754 | 0.0368 |
| GHD | rs5918762 | AR | BMI SDS Change | Dominant | 0.036754 | 0.0368 |
| GHD | rs3218097 | CCND3 | BMI SDS Change | Genotype | 0.002086 | 0.0021 |
| GHD | rs3218097 | CCND3 | BMI SDS Change | Recessive | 0.039911 | 0.0399 |
| GHD | rs10459592 | CYP19A1 | Height Change (cm) | Recessive | 0.002867 | 0.0430 |
| GHD | rs4130113 | GHR | BMI SDS Change | Genotype | 0.001653 | 0.0364 |
| GHD | rs2267723 | GHRHR | Height Velocity SDS | Dominant | 0.004665 | 0.0280 |
| GHD | rs1024531 | GRB10 | Height Change (cm) | Genotype | 0.000476 | 0.0100 |
| GHD | rs1024531 | GRB10 | Height Change (cm) | Recessive | 0.000576 | 0.0121 |
| GHD | rs12536500 | GRB10 | Height Change (cm) | Recessive | 0.001206 | 0.0253 |
| GHD | rs933360 | GRB10 | Height Change (cm) | Recessive | 0.002132 | 0.0448 |
| GHD | rs1024531 | GRB10 | Height SDS Change | Genotype | 0.002045 | 0.0429 |

TABLE 4A-continued

SNPs associated through continuous analysis.

| Condition | SNP ID | Gene | Endpoint | Model | Nominal p-value | Adjusted p-value |
|---|---|---|---|---|---|---|
| GHD | rs12536500 | GRB10 | Height SDS Change | Recessive | 0.002119 | 0.0445 |
| GHD | rs4789182 | GRB2 | Height SDS Change | Recessive | 0.010576 | 0.0317 |
| GHD | rs10255707 | IGFBP3 | Height Change (cm) | Dominant | 0.005556 | 0.0278 |
| GHD | rs3110697 | IGFBP3 | Height Change (cm) | Dominant | 0.002334 | 0.0117 |
| GHD | rs3110697 | IGFBP3 | Height Change (cm) | Genotype | 0.008833 | 0.0442 |
| GHD | rs10255707 | IGFBP3 | Height SDS Change | Dominant | 0.003510 | 0.0175 |
| GHD | rs3110697 | IGFBP3 | Height SDS Change | Dominant | 0.002062 | 0.0103 |
| GHD | rs10255707 | IGFBP3 | Height SDS Change | Genotype | 0.007580 | 0.0379 |
| GHD | rs3110697 | IGFBP3 | Height SDS Change | Genotype | 0.007116 | 0.0356 |
| GHD | rs10255707 | IGFBP3 | Height Velocity SDS | Dominant | 0.002440 | 0.0122 |
| GHD | rs3110697 | IGFBP3 | Height Velocity SDS | Dominant | 0.000252 | 0.0013 |
| GHD | rs10255707 | IGFBP3 | Height Velocity SDS | Genotype | 0.003490 | 0.0175 |
| GHD | rs3110697 | IGFBP3 | Height Velocity SDS | Genotype | 0.001009 | 0.0050 |
| GHD | rs2276048 | INPPL1 | Height Change (cm) | Genotype | 0.049741 | 0.0497 |
| GHD | rs2276048 | INPPL1 | Height Change (cm) | Recessive | 0.025435 | 0.0254 |
| GHD | rs2276048 | INPPL1 | Height Velocity SDS | Dominant | 0.049520 | 0.0495 |
| GHD | rs3842748 | INS | Height Velocity SDS | Dominant | 0.039409 | 0.0394 |
| GHD | rs7254921 | INSR | BMI SDS Change | Dominant | 0.000402 | 0.0125 |
| GHD | rs10974947 | JAK2 | BMI SDS Change | Genotype | 0.001930 | 0.0251 |
| GHD | rs2274471 | JAK2 | BMI SDS Change | Recessive | 0.002113 | 0.0275 |
| GHD | rs10842514 | KRAS | BMI SDS Change | Dominant | 0.006146 | 0.0369 |
| GHD | rs11047912 | KRAS | Height Velocity SDS | Genotype | 0.003018 | 0.0181 |
| GHD | rs7651265 | PIK3CA | Height SDS Change | Recessive | 0.005093 | 0.0407 |
| GHD | 24531_rs7475 | PPP1CB | BMI SDS Change | Dominant | 0.006297 | 0.0441 |
| GHD | rs2045886 | PPP1CB | BMI SDS Change | Dominant | 0.006297 | 0.0441 |
| GHD | rs6725177 | PPP1CB | BMI SDS Change | Dominant | 0.006297 | 0.0441 |
| GHD | rs6550976 | RARB | Height SDS Change | Genotype | 0.000347 | 0.0160 |

TABLE 4A-continued

SNPs associated through continuous analysis.

| Condition | SNP ID | Gene | Endpoint | Model | Nominal p-value | Adjusted p-value |
|---|---|---|---|---|---|---|
| GHD | rs4845401 | SHC1 | BMI SDS Change | Dominant | 0.038479 | 0.0385 |
| GHD | rs2895543 | SHOX | Height Velocity SDS | Dominant | 0.015001 | 0.0150 |
| GHD | rs1498708 | SOCS2 | BMI SDS Change | Dominant | 0.040903 | 0.0409 |
| GHD | rs1498708 | SOCS2 | BMI SDS Change | Genotype | 0.041882 | 0.0419 |
| GHD | rs1498708 | SOCS2 | BMI SDS Change | Recessive | 0.033467 | 0.0335 |
| GHD | rs1498708 | SOCS2 | Height Velocity SDS | Dominant | 0.011188 | 0.0112 |
| GHD | rs1498708 | SOCS2 | Height Velocity SDS | Genotype | 0.040006 | 0.0400 |
| GHD | rs2888586 | SOS1 | Height Change (cm) | Recessive | 0.009518 | 0.0476 |
| GHD | rs8017367 | SOS2 | Height Velocity SDS | Recessive | 0.002867 | 0.0229 |
| GHD | rs958686 | TGFA | Height Change (cm) | Genotype | 0.001594 | 0.0351 |
| GHD | rs958686 | TGFA | Height Change (cm) | Recessive | 0.002091 | 0.0460 |
| GHD | rs2909430 | TP53 | Height Change (cm) | Recessive | 0.013801 | 0.0414 |
| GHD | rs2909430 | TP53 | Height Velocity SDS | Genotype | 0.004619 | 0.0139 |
| GHD | rs2909430 | TP53 | Height Velocity SDS | Recessive | 0.002447 | 0.0073 |
| GHD | rs16923242 | WT1 | BMI SDS Change | Dominant | 0.002672 | 0.0321 |
| GHD | rs3930513 | WT1 | BMI SDS Change | Dominant | 0.000507 | 0.0061 |
| GHD | rs6484577 | WT1 | BMI SDS Change | Dominant | 0.001322 | 0.0159 |
| GHD | rs3930513 | WT1 | BMI SDS Change | Genotype | 0.001524 | 0.0183 |
| TS | rs603965 | CCND1 | BMI SDS Change from Baseline at Year 1 | Dominant | 0.016995466 | 0.034 |
| TS | rs3218097 | CCND3 | Height Velocity SDS at Year 1 | Dominant | 0.040155978 | 0.0402 |
| TS | rs2347867 | ESR1 | Height Velocity SDS at Year 1 | Dominant | 0.000291899 | 0.0128 |
| TS | rs12579073 | KRAS | Height Change (cm) From Baseline at Year 1 | Genotype | 0.007678668 | 0.0461 |
| TS | rs3845395 | LHX4 | Height Change (cm) From Baseline at Year 1 | Recessive | 0.00230756 | 0.0485 |

TABLE 4A-continued

SNPs associated through continuous analysis.

| Condition | SNP ID | Gene | Endpoint | Model | Nominal p-value | Adjusted p-value |
|---|---|---|---|---|---|---|
| TS | rs12667819 | PIK3CG | BMI SDS Change from Baseline at Year 1 | Recessive | 0.0111136 | 0.0445 |
| TS | rs751210 | SLC2A1 | BMI SDS Change from Baseline at Year 1 | Genotype | 0.001867234 | 0.0149 |
| TS | rs5435 | SLC2A4 | BMI SDS Change from Baseline at Year 1 | Genotype | 0.034804327 | 0.0348 |
| TS | rs2168043 | SOS1 | Height SDS Change from Baseline at Year | Recessive | 0.008248227 | 0.0412 |
| TS | rs378322 | TGFA | BMI SDS Change from Baseline at Year 1 | Genotype | 0.000849322 | 0.0187 |
| TS | rs378322 | TGFA | BMI SDS Change from Baseline at Year 1 | Recessive | 0.000849322 | 0.0187 |
| TS | rs503314 | TGFA | Height SDS Change from Baseline at Year | Dominant | 0.002147721 | 0.0472 |

TABLE 4B

Characteristics of SNPs Associated through Continuous Analyses

| Condition | SNP ID | Gene | Endpoint | Model | MAF | SNPs per gene | LD blocks per gene |
|---|---|---|---|---|---|---|---|
| GHD | rs5918757 | AR | BMI SDS Change | Dominant | 20.7% | 2 | 1 |
| GHD | rs5918762 | AR | BMI SDS Change | Dominant | 20.7% | 2 | 1 |
| GHD | rs3218097 | CCND3 | BMI SDS Change | Genotype | 21.6% | 1 | 1 |
| GHD | rs3218097 | CCND3 | BMI SDS Change | Recessive | 21.6% | 1 | 1 |
| GHD | Rs10459592 | CYP19A1 | Height Change (cm) | Recessive | 45.0% | 18 | 15 |
| GHD | rs4130113 | GHR | BMI SDS Change | Genotype | 41.7% | 45 | 22 |
| GHD | rs2267723 | GHRHR | Height Velocity SDS | Dominant | 41.4% | 7 | 6 |
| GHD | rs1024531 | GRB10 | Height Change (cm) | Genotype | 25.0% | 30 | 21 |
| GHD | rs1024531 | GRB10 | Height Change (cm) | Recessive | 25.0% | 30 | 21 |
| GHD | Rs12536500 | GRB10 | Height Change (cm) | Recessive | 20.0% | 30 | 21 |

TABLE 4B-continued

Characteristics of SNPs Associated through Continuous Analyses

| Condition | SNP ID | Gene | Endpoint | Model | MAF | SNPs per gene | LD blocks per gene |
|---|---|---|---|---|---|---|---|
| GHD | rs933360 | GRB10 | Height Change (cm) | Recessive | 20.9% | 30 | 21 |
| GHD | rs1024531 | GRB10 | Height SDS Change | Genotype | 25.0% | 30 | 21 |
| GHD | Rs12536500 | GRB10 | Height SDS Change | Recessive | 20.0% | 30 | 21 |
| GHD | rs4789182 | GRB2 | Height SDS Change | Recessive | 30.0% | 5 | 3 |
| GHD | Rs10255707 | IGFBP3 | Height Change (cm) | Dominant | 23.3% | 6 | 5 |
| GHD | rs3110697 | IGFBP3 | Height Change (cm) | Dominant | 35.8% | 6 | 5 |
| GHD | rs3110697 | IGFBP3 | Height Change (cm) | Genotype | 35.8% | 6 | 5 |
| GHD | Rs10255707 | IGFBP3 | Height SDS Change | Dominant | 23.3% | 6 | 5 |
| GHD | rs3110697 | IGFBP3 | Height SDS Change | Dominant | 35.8% | 6 | 5 |
| GHD | Rs10255707 | IGFBP3 | Height SDS Change | Genotype | 23.3% | 6 | 5 |
| GHD | rs3110697 | IGFBP3 | Height SDS Change | Genotype | 35.8% | 6 | 5 |
| GHD | rs10255707 | IGFBP3 | Height Velocity SDS | Dominant | 23.3% | 6 | 5 |
| GHD | rs3110697 | IGFBP3 | Height Velocity SDS | Dominant | 35.8% | 6 | 5 |
| GHD | rs10255707 | IGFBP3 | Height Velocity SDS | Genotype | 23.3% | 6 | 5 |
| GHD | rs3110697 | IGFBP3 | Height Velocity SDS | Genotype | 35.8% | 6 | 5 |
| GHD | rs2276048 | INPPL1 | Height Change (cm) | Genotype | 19.1% | 1 | 1 |
| GHD | rs2276048 | INPPL1 | Height Change (cm) | Recessive | 19.1% | 1 | 1 |
| GHD | rs2276048 | INPPL1 | Height Velocity SDS | Dominant | 19.1% | 1 | 1 |
| GHD | rs3842748 | INS | Height Velocity SDS | Dominant | 17.7% | 1 | 1 |
| GHD | rs7254921 | INSR | BMI SDS Change | Dominant | 47.2% | 33 | 31 |
| GHD | rs10974947 | JAK2 | BMI SDS Change | Genotype | 32.6% | 41 | 13 |
| GHD | rs2274471 | JAK2 | BMI SDS Change | Recessive | 32.9% | 41 | 13 |
| GHD | rs10842514 | KRAS | BMI SDS Change | Dominant | 42.7% | 9 | 6 |
| GHD | rs11047912 | KRAS | Height Velocity SDS | Genotype | 29.5% | 9 | 6 |
| GHD | rs7651265 | PIK3CA | Height SDS Change | Recessive | 15.9% | 20 | 8 |
| GHD | 24531_rs7475 | PPP1CB | BMI SDS Change | Dominant | 46.8% | 11 | 7 |
| GHD | rs2045886 | PPP1CB | BMI SDS Change | Dominant | 46.8% | 11 | 7 |
| GHD | rs6725177 | PPP1CB | BMI SDS Change | Dominant | 48.2% | 11 | 7 |
| GHD | rs6550976 | RARB | Height SDS Change | Genotype | 39.1% | 47 | 46 |
| GHD | rs4845401 | SHC1 | BMI SDS Change | Dominant | 47.2% | 1 | 1 |

TABLE 4B-continued

Characteristics of SNPs Associated through Continuous Analyses

| Condition | SNP ID | Gene | Endpoint | Model | MAF | SNPs per gene | LD blocks per gene |
|---|---|---|---|---|---|---|---|
| GHD | rs2895543 | SHOX | Height Velocity SDS | Dominant | 22.3% | 1 | 1 |
| GHD | rs1498708 | SOCS2 | BMI SDS Change | Dominant | 15.4% | 1 | 1 |
| GHD | rs1498708 | SOCS2 | BMI SDS Change | Genotype | 15.4% | 1 | 1 |
| GHD | rs1498708 | SOCS2 | BMI SDS Change | Recessive | 15.4% | 1 | 1 |
| GHD | rs1498708 | SOCS2 | Height Velocity SDS | Dominant | 15.3% | 1 | 1 |
| GHD | rs1498708 | SOCS2 | Height Velocity SDS | Genotype | 15.3% | 1 | 1 |
| GHD | rs2888586 | SOS1 | Height Change (cm) | Recessive | 43.6% | 21 | 5 |
| GHD | rs8017367 | SOS2 | Height Velocity SDS | Recessive | 27.3% | 9 | 8 |
| GHD | rs958686 | TGFA | Height Change (cm) | Genotype | 40.0% | 32 | 22 |
| GHD | rs958686 | TGFA | Height Change (cm) | Recessive | 40.0% | 32 | 22 |
| GHD | rs2909430 | TP53 | Height Change (cm) | Recessive | 15.5% | 3 | 3 |
| GHD | rs2909430 | TP53 | Height Velocity SDS | Genotype | 15.5% | 3 | 3 |
| GHD | rs2909430 | TP53 | Height Velocity SDS | Recessive | 15.5% | 3 | 3 |
| GHD | rs16923242 | WT1 | BMI SDS Change | Dominant | 27.5% | 12 | 12 |
| GHD | rs3930513 | WT1 | BMI SDS Change | Dominant | 44.9% | 12 | 12 |
| GHD | rs6484577 | WT1 | BMI SDS Change | Dominant | 36.2% | 12 | 12 |
| GHD | rs3930513 | WT1 | BMI SDS Change | Genotype | 44.9% | 12 | 12 |
| TS | rs603965 | CCND1 | BMI SDS Change from Baseline at Year 1 | Dominant | 45.8% | 2 | 2 |
| TS | rs3218097 | CCND3 | Height Velocity SDS at Year 1 | Dominant | 28.3% | 1 | 1 |
| TS | rs2347867 | ESR1 | Height Velocity SDS at Year 1 | Dominant | 43.3% | 80 | 44 |
| TS | rs12579073 | KRAS | Height Change (cm) From Baseline at Year 1 | Genotype | 43.3% | 9 | 6 |
| TS | rs3845395 | LHX4 | Height Change (cm) From Baseline at Year 1 | Recessive | 30.8% | 22 | 21 |
| TS | rs12667819 | PIK3CG | BMI SDS Change from Baseline at Year 1 | Recessive | 42.5% | 5 | 4 |

TABLE 4B-continued

Characteristics of SNPs Associated through Continuous Analyses

| Condition | SNP ID | Gene | Endpoint | Model | MAF | SNPs per gene | LD blocks per gene |
|---|---|---|---|---|---|---|---|
| TS | rs751210 | SLC2A1 | BMI SDS Change from Baseline at Year 1 | Genotype | 30.8% | 11 | 8 |
| TS | rs5435 | SLC2A4 | BMI SDS Change from Baseline at Year 1 | Genotype | 35.8% | 1 | 1 |
| TS | rs2168043 | SOS1 | Height SDS Change from Baseline at Year | Recessive | 17.5% | 37 | 5 |
| TS | rs378322 | TGFA | BMI SDS Change from Baseline at Year 1 | Genotype | 10.0% | 32 | 22 |
| TS | rs378322 | TGFA | BMI SDS Change from Baseline at Year 1 | Recessive | 10.0% | 32 | 22 |
| TS | rs503314 | TGFA | Height SDS Change from Baseline at Year | Dominant | 33.3% | 32 | 22 |

The invention claimed is:

1. A method of treating Growth Hormone Deficiency (GHD) or Turner Syndrome (TS) in an individual in need thereof, the method comprising the steps of:
   a) determining in a DNA sample of the individual whether in GRB10 rs933360 either of the TT, CC or TC genotype is present;
   b) predicting from the presence of the CC or TC genotype in GRB10 rs933360 an intermediate or low change in height in cm from baseline or predicting from the presence of the TT genotype in GRB10 rs933360 a high change in height in cm from baseline; and
   c) administering a standard dose of growth hormone to an individual having the TT genotype in GRB10 rs933360, or administering an increased dose of growth hormone, as compared to a standard dose, or a long acting analog of growth hormone to an individual having in GRB10 rs933360 either the CC or TC genotype.

2. A method of treating Growth Hormone Deficiency (GHD) or Turner Syndrome (TS) in an individual in need thereof, the method comprising the steps of:
   a) administering growth hormone to said individual for a period of one year;
   b) determining in a DNA sample of the individual whether in GRB10 rs933360 the TT, CC, or TC genotype is present;
   c) predicting from the presence of the TT, CC, or TC genotype in GRB10 rs933360 a high, intermediate or low change in height in cm from baseline; and
   d) administering a standard dose of growth hormone to an individual having the TT genotype in GRB10 rs933360, or administering an increased dose of growth hormone, as compared to a standard dose, or a long acting analog of growth hormone to an individual having in GRB10 rs933360 either the CC or TC genotype.

* * * * *

UNITED STATES PATENT AND TRADEMARK OFFICE
CERTIFICATE OF CORRECTION

PATENT NO.         : 9,175,347 B2
APPLICATION NO.    : 13/819058
DATED              : November 3, 2015
INVENTOR(S)        : Pascal Croteau et al.

Page 1 of 1

It is certified that error appears in the above-identified patent and that said Letters Patent is hereby corrected as shown below:

Specification

Column 17,
Line 2, "STAT cluster" should read --STAT_cluster--.
Line 5, "STAT cluster" should read --STAT_cluster--.

Signed and Sealed this
Fifth Day of April, 2016

Michelle K. Lee
*Director of the United States Patent and Trademark Office*